United States Patent
Farina et al.

[11] Patent Number: 5,981,525
[45] Date of Patent: Nov. 9, 1999

[54] INDOLE DERIVATIVES USEFUL IN THE TREATMENT OF OSTEOPOROSIS

[75] Inventors: Carlo Farina; Stefania Gagliardi; Carlo Parini; Mario Pinza, all of Milan, Italy; Guy Marguerite Marie Gerard Nadler; Marcel Jean-Marie Morvan, both of Rennes, France

[73] Assignee: SmithKline Beecham Corporation, Philadelphia, Pa.

[21] Appl. No.: 08/860,760

[22] PCT Filed: Jan. 8, 1996

[86] PCT No.: PCT/EP96/00157

§ 371 Date: Oct. 9, 1997

§ 102(e) Date: Oct. 9, 1997

[87] PCT Pub. No.: WO96/21644

PCT Pub. Date: Jul. 18, 1996

[30] Foreign Application Priority Data

Jan. 10, 1995 [IT] Italy .................. MI95A0030
Aug. 1, 1995 [IT] Italy .................. MI95A1687

[51] Int. Cl.[6] .............. C07D 209/14; C07D 209/12; C07D 401/12; C07D 417/12
[52] U.S. Cl. ............ 514/235.2; 514/247; 514/255; 514/256; 514/266; 514/258; 514/323; 514/339; 514/397; 514/419; 544/143; 544/238; 544/262; 544/277; 544/333; 544/373; 546/133; 546/146; 546/175; 546/201; 546/277.4
[58] Field of Search ................ 514/419, 235.2, 514/255, 256, 339; 548/494, 495, 496, 181, 414, 468, 312.1; 544/143, 373, 333, 262, 277, 238; 546/133, 146, 175, 201, 277.4

[56] References Cited

U.S. PATENT DOCUMENTS 5,312,928  5/1994  Goldin et al. .............. 548/495

FOREIGN PATENT DOCUMENTS 0 449 196  2/1991  European Pat. Off. .

*Primary Examiner*—Mukund J. Shah
*Assistant Examiner*—Deepak R. Rao
*Attorney, Agent, or Firm*—Mark E. McCarthy; Stephen Venetianer; Charles M. Kinzig

[57] ABSTRACT

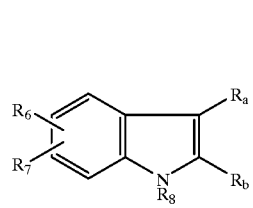

(I)

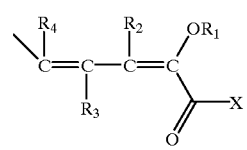

(a)

A compound of formula (I) or a salt thereof, or a solvate thereof, wherein either (i) Ra represents a group $R_5$ which is hydrogen, alkyl or optionally substituted aryl and $R_5$ represents a moiety of formula (a); wherein X represents a hydroxy or an alkoxy group wherein the alkyl group may be substituted or unsubstituted or X represents a group $NR_sR_t$ wherein $R_s$ and $R_t$ each independently represent hydrogen, alkyl, substituted alkyl, optionally substituted alkenyl, optionally substituted aryl, optionally substituted arylalkyl, an optionally substituted heterocyclic group or an optionally substituted heterocyclylalkyl group, or $R_s$ and $R_t$ together may form a heterocyclic group; $R_1$ represents an alkyl or a substituted or unsubstituted aryl group; and $R_2$, $R_3$ and $R_4$ each independently represent hydrogen, alkyl, aryl or substituted aryl or (ii) $R_a$ represents a moiety of the above defined formula (a) and $R_b$ represents the above defined $R_5$; $R_6$ and $R_7$ each independently represents hydrogen, hydroxy, amino, alkoxy, optionally substituted aryloxy, optionally substituted benzyloxy, alkylamino, dialkylamino, halo, trifluoromethyl, trifluoromethoxy, nitro, alkyl, carboxy, carbalkoxy, carbamoyl, alkylcarbamoyl, or $R_6$ and $R_7$ together represent methylenedioxy, carbonyldioxy or carbonyldiamino; and $R_8$ represents hydrogen, hydroxy, allanoyl, alkyl, aminoalkyl, hydroxyalkyl, carboxyalkyl, carbalkoxyalkyl, carbamoyl or aminosulphonyl; a process for the preparation of such a compound, a pharmaceutical composition comprising such a compound and the use of such a compound in medicine.

13 Claims, No Drawings

INDOLE DERIVATIVES USEFUL IN THE TREATMENT OF OSTEOPOROSIS

This invention relates to certain novel compounds, to a process for preparing such compounds, to pharmaceutical compositions containing such compounds and to the use of such compounds and compositions in medicine.

It has surprisingly been discovered that certain indole derivatives are indicated to reduce bone resorption by inhibiting osteoclast H$^+$-ATPase and are therefore of potential use for the treatment and/or prophylaxis of osteoporosis and related osteopenic diseases. These compounds are also considered to possess anti-tumour activity, antiviral activity (for example against Semliki Forest, Vesicular Stomatitis, Newcastle Disease, Influenza A and B, HIV viruses), antiulcer activity (for example the compounds may be useful for the treatment of chronic gastritis and peptic ulcer induced by *Helicobacter pylori*), immunosupressant activity, antilipidemic activity, antiatherosclerotic activity and to be useful for the treatment of AIDS and Alzheimer's disease. In a further aspect, these compounds are also considered useful in inhibiting angiogenesis, i.e. the formation of new blood vessels which is observed in various types of pathological conditions (angiogenic diseases) such as rheumatoid arthritis, diabetic retinopathy, psoriasis and solid tumours.

Accordingly, the present invention provides a compound of formula (I):

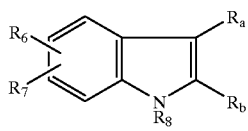

(I)

or a salt thereof, or a solvate thereof, wherein
either: (i) Ra represents a group $R_5$ which is hydrogen, alkyl or optionally substituted aryl and Rb represents a moiety of formula (a):

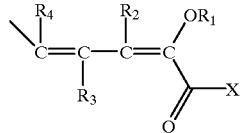

(a)

wherein X represents a hydroxy or an alkoxy group wherein the alkyl group may be substituted or unsubstituted or X represents a group $NR_sR_t$ wherein $R_s$ and $R_t$ each independently represent hydrogen, alkyl, substituted alkyl, optionally substituted alkenyl, optionally substituted aryl, optionally substituted arylalkyl, an optionally substituted heterocyclic group or an optionally substituted heterocyclylalkyl group, or $R_s$ and $R_t$ together may form a heterocyclic group; $R_1$ represents an alkyl or a substituted or unsubstituted aryl group; and $R_2$, $R_3$ and $R_4$ each independently represent hydrogen, alkyl, aryl or substituted aryl or (ii) $R_a$ represents a moiety of the above defined formula (a) and $R_b$ represents the above defined $R_5$;

$R_6$ and $R_7$ each independently represents hydrogen, hydroxy, amino, alkoxy, optionally substituted aryloxy, optionally substituted benzyloxy, alkylamino, dialkylamino, halo, trifluoromethyl, trifluoromethoxy, nitro, alkyl, carboxy, carbalkoxy, carbamoyl, alkylcarbamoyl, or $R_6$ and $R_7$ together represent methylenedioxy, carbonyldioxy or carbonyldiamino; and $R_8$ represents hydrogen, hydroxy, alkanoyl, alkyl, aminoalkyl, hydroxyalkyl, carboxyalkyl, carbalkoxyalkyl, carbamoyl or aminosulphonyl.

In one aspect, and preferably, Ra represents a group $R_5$ which is hydrogen, alkyl or optionally substituted aryl and Rb represents a moiety of formula (a).

In a further aspect, $R_a$ represents a moiety of the above defined formula (a) and $R_b$ represents the above defined R5.

In one aspect $R_1$ represents alkyl or substituted or unsubstituted phenyl.

Suitably, $R_1$ represents a $C_{1-4}$-alkyl group, for example methyl or ethyl.

Preferably, $R_1$ represents methyl.

In one aspect, $R_2$, $R_3$ and $R_4$ each independently represent hydrogen, alkyl or phenyl.

Examples of $R_2$ include hydrogen and methyl.

Suitably, $R_2$ represents hydrogen.

Examples of $R_3$ include hydrogen and ethyl.

Suitably, $R_3$ represents hydrogen.

Examples of $R_4$ include hydrogen, propyl and phenyl.

Suitably, $R_4$ represents hydrogen.

In one aspect, $R_5$ is hydrogen, alkyl or substituted or, suitably, unsubstituted phenyl.

Examples of $R_5$ include hydrogen, ethyl and 4-methoxyphenyl.

Suitably, $R_5$ is hydrogen.

In one aspect $R_6$ and $R_7$ each independently represents hydrogen, hydroxy, amino, alkoxy, optionally substituted phenyloxy, optionally substituted benzyloxy, alkylamino, dialkylamino, halo, trifluoromethyl, nitro, alkyl, carboxy, carbalkoxy, carbamoyl, alkylcarbamoyl, or $R_6$ and $R_7$ together represent methylenedioxy, carbonyldioxy or carbonyldiamino.

Suitably, $R_6$ and $R_7$ each independently represents alkoxy, halo, trifluoromethyl, nitro, and alkyl.

When $R_6$ or $R_7$ represents alkoxy, said alkoxy group is suitably a $C_{1-6}$ alkoxy for example methoxy.

When $R_6$ or $R_7$ represents halo, said halo group is suitably a fluoro or chloro group.

When $R_6$ or $R_7$ represents alkyl, said alkyl group is suitably a $C_{1-6}$ alkyl for a example butyl group.

Suitable positions for substitution for $R_6$ or $R_7$ are the 4, 5, 6 or 7 position, favourably the 5 or 6 position.

When neither of $R_6$ or $R_7$ represent hydrogen then favoured positions for bis-substitution are 5 and 6 positions.

Favoured values for $R_6$ and $R_7$ are hydrogen, halo, trifluoromethyl and alkoxy.

In one aspect $R_6$ is hydrogen and $R_6$ or $R_7$ represents hydrogen alkoxy, halo, nitro, trifluoromethyl and alkyl.

In a further aspect $R_6$ and $R_7$ are each selected from hydrogen, halo and alkoxy, examples include: $R_6$ is halo and $R_7$ is halo; $R_6$ is halo and $R_7$ is alkyl; $R_6$ is alkoxy and $R_7$ is alkoxy.

In a preferred aspect $R_6$ is halo, especially 5-halo, and $R_7$ is halo, especially 6-halo.

Most preferably $R_6$ is chloro, especially 5-chloro, and $R_7$ is chloro, especially 6-chloro.

Examples of $R_8$ include hydrogen, methyl and t-butoxycarbonylmethyl.

Suitably, $R_8$ represents hydrogen.

When X represents an alkoxy group, the alkyl group thereof is preferably an unsubstituted alkyl group.

Suitably, X represents the above defined group N $R_s$ $R_t$.

In one aspect, $R_s$ and $R_t$ each independently represent hydrogen, alkyl, substituted alkyl, optionally substituted alkenyl, optionally substituted aryl, optionally substituted arylalkyl, an optionally substituted heterocyclic group or an optionally substituted heterocyclylalkyl group.

In a further aspect, $R_s$ and $R_t$ together represent a heterocyclic group.

When $R_s$ or $R_t$ represent alkyl or substituted alkyl, suitable alkyl groups are $C_{1-6}$ alkyl groups, for example $C_1$, $C_2$, $C_3$, $C_4$ and $C_5$ alkyl groups, favourably ethyl, propyl or butyl.

When $R_s$ or $R_t$ represent substituted alkyl, favoured groups are 2-(dialkylamino)ethyl or 3-(dialkylamino)propyl or 4-(dialkylamino)butyl or heterocyclylmethyl or heterocyclylethyl or heterocyclylpropyl groups.

When $R_s$ or $R_t$ represent alkenyl or substituted alkenyl, suitable alkenyl groups are $C_{2-6}$ alkenyl groups, for example a $C_5$ alkenyl group.

When $R_s$ or $R_t$ represent aryl or substituted aryl, suitable aryl groups are phenyl groups.

In one favoured aspect $R_t$ is hydrogen.

Suitable heterocyclic groups include single ring saturated heterocyclic groups, single ring unsaturated heterocyclic groups, fused ring heterocyclic groups.

Fused ring heterocyclic groups include spiro heterocyclic groups.

Suitable single ring unsaturated heterocyclic groups comprise 5-, 6- or 7- membered rings.

Suitable 5-membered single ring unsaturated heterocyclic groups are furanyl, thienyl, pyrrolyl, pyrazolyl, imidazolyl, triazolyl, tetrazolyl, oxazolyl, isoxazolyl, furazanyl, thiazolyl and isothiazolyl groups; or partially saturated derivatives thereof, such as 4,5-dihydro-1,3-thiazol-2-yl, 1H-imidazolinyl, pyrrolinyl, pyrazolinyl, oxazolinyl, isoxazolinyl, thiazolinyl groups.

Suitable 6-membered single ring unsaturated heterocyclic groups are pyridyl, pyrimidinyl, pyridazinyl, pyrazinyl, triazinyl, tetrazinyl, 1,2- or 1,3- or 1,4-oxazinyl, 1,2- or 1,3- or 1,4-thiazinyl and pyranyl groups, or partially saturated derivatives thereof such as 1,2- or 1,3- or 1,4- dihydrooxazinyl, 1,4dihydropyridyl, dihydropyridazinyl, dihydropyrazinyl or dihydropyrimidinyl.

Suitable 7-membered single ring unsaturated heterocyclic groups are azepinyl, oxepinyl, diazepinyl, thiazepinyl, oxazepinyl or partially saturated derivatives thereof.

Suitable, single ring saturated heterocyclic groups comprise 5-, 6- or 7- membered rings.

Suitable 5-membered single ring saturated heterocyclic groups are pyrrolidinyl, imidazolidinyl, pyrazolidinyl, oxazolidinyl, isoxazolidinyl and terahydrofuranyl groups.

Suitable 6-membered single ring saturated heterocyclic groups are piperidinyl, piperazinyl, tetrahydropyranyl, 1,3-dioxacyclohexyl, tetrahydro- 1,4-thiazinyl, morpholinyl and morpholino groups.

Suitable 7-membered single ring saturated heterocyclic groups are hexamethyleniminyl, oxepanyl and thiepanyl.

Suitable fused ring heterocyclic groups include fused saturated rings, fused unsaturated rings and saturated rings fused to unsaturated rings.

Suitable groups having fused saturated rings are quinuclidyl, 8-azabicyclo[3.2.1]octyl, 9-azabicyclo[3.3.1]nonyl, 1-azabicyclo[3.3.3]undecyl, 1,9-diazabicyclo[3.3.1]nonyl and 1,5-diazabicyclo[3.3.1]nonyl groups.

Suitable groups having fused unsaturated rings are pyrazo[3.4-d]pyrimidinyl, 1,2,5-thiadiazolo[3,4-b]pyridyl, isoxazolo[4,5-b]pyridyl, thiazolo[4,5-b]pyridyl, oxazolo[4,5-d]pyrimidinyl, 7H-purin-2-yl, quinolyl, isoquinolyl, benzo[b]thienyl, benzofuranyl, isobenzofuranyl, benzoxazolyl, benzothiazolyl, indolizinyl, indolyl, isoindolyl, indazolyl, phthalazinyl, naphthyridinyl, quinoxalinyl, quinazolinyl, cinnolinyl, pteridinyl and β-carbolinyl groups.

Suitable groups having saturated rings fused to unsaturated rings includes groups which are fused to benzene rings such as tetrahydroquinolyl, 4H-quinolizinyl, tetrahydroisoquinolyl, dihydrobenzofuryl, chromenyl, chromanyl, isochromanyl, indolinyl and isoindolinyl groups.

Suitable spiro heterocyclic groups include oxaspiro[4.5]decyl, azaspiro[4.5]decyl, 1,2,4-triazaspiro[5.5]undecyl, 1,4-dioxa-9-azaspiro[4.7]dodecyl and 1-azaspiro[5.5]undecyl.

Suitable values for $R_s$ include hydrogen, $C_{1-5}$ alkyl, mono- di- and tri-hydroxyallyl, alkoxyalkyl, carboxyalkyl, carbalkoxyalkyl, bisphosphonylalkyl, (substituted)amnino-carboxyallkyl, biscarbethoxy-hydroxyalkenyl, dialkylaminoalkyl, pyridyl, mono- di- and tri-alkoxypyridyl, dialkylaminoalkoxypyridyl, aryloxypyridyl, aminopyridyl, substituted piperazinyl, quinuclidyl, saturated heterocyclylalkyl, substituted piperidinyl, (di)azabicycloalkyl, substituted phenyl, substituted benzyl, substituted phenylethyl, 1-imidazolylalkyl, thiazolinyl, (2-tetrahydroisoquinolinyl)alkyl, 1H-pyrazolo[3,4-d]pyrimidin-4-yl, 7H-purin-2-yl, pyridylalkyl, (2-pyrimidinyl)piperazin-1-ylalkyl, substituted pyridazinyl, substituted pyrazinyl, substituted pyrimidinyl, quinolyl, isoquinolyl, tetrahydroisoquinolyl, tetrahydroquinolyl.

Preferred values for $R_s$ include diethylaminopropyl, 3-amino-3-carboxypropyl, 4-amino-4-carboxybutyl, 3-pyridyl, diethylaminoethyl, 3-quinuclidyl (or 1-azabicyclo[2.2.2]octan-3-yl), morpholinopropyl, piperidinopropyl, 1-methyl-2-pyrrolidinylethyl, 2,2,6,6-tetramethyl4-piperidinyl, 2-methoxy-5-pyridyl, 2-methylpiperidinopropyl, 8-methyl-8-azabicyclo[3.2.1]oct-3β-yl, 1-methyl-4-piperidinyl, 1H-pyrazolo[3,4]-pyrimidin-4-yl, 2,2,5,5-tetramethyl-3-pyrrolidinylmethyl, 2-methoxy-4-pyridyl, 1-ethyl-3-piperidinyl, 3-[4-(2-pyrimidinyl)piperazin-1-yl]propyl.

Suitable values for $R_t$ include hydrogen, methyl, $C_{2-5}$ alkyl, 2-hydroxyethyl, 2-methoxyethyl, carboxymethyl, carbomethoxymethyl, 4-hydroxybutyl and 2,3-dihydroxypropyl, especially hydrogen.

In one preferred aspect $R_t$ represents hydrogen.

Particular examples of the invention are the compounds of example numbers: 4, 6, 26, 33, 34, 44, 46, 50, 51, 53, 54, 56, 57, 59, 64, 66, 70, 71, 84, 87, 96, 97, 100 and 103.

As used herein, the term "alkyl" includes straight or branched chain alkyl groups having from 1 to 12, suitably 1 to 6, preferably 1 to 4, carbon atoms, such as methyl, ethyl, n- and isopropyl and n- iso-, tert-butyl and pentyl groups, and also includes such alkyl groups when forming part of other groups such as alkoxy or alkanoyl groups.

Suitable optional substituents for any alkyl group include hydroxy; alkoxy; a group of formula $NR_uR_v$ wherein $R_u$ and $R_v$ each independently represent hydrogen, optionally substituted alkyl, optionally substituted cycloalkyl, optionally substituted aryl, optionally substituted arylalkyl, optionally substituted heterocyclyl, optionally substituted heterocyclylalkyl, carboxy, carboxyalkyl, or alkoxycarbonyl, nitro, or $R_u$ and $R_v$ together form an optionally substituted heterocyclic ring; carboxy; alkoxycarbonyl; alkoxycarbonylalkyl; alkylcarbonyloxy; alkylcarbonyl; mono-and di-alkylphosphonate; optionally substituted aryl; and optionally substituted heterocyclyl.

A preferred alkyl substituent is $NR_uR_v$, wherein $R_u$ and $R_v$ each independently represent hydrogen, optionally substituted aryl, optionally substituted arylalkyl, optionally substituted heterocyclyl, optionally substituted heterocyclylalkyl or $R_u$ and $R_v$ together form an optionally substituted heterocyclic ring.

When $R_s$ or $R_t$ represents substituted alkyl, especially $C_{1-4}$ alkyl, particular values are the moieties of formulae (a), (b), (c), (d) and (e):

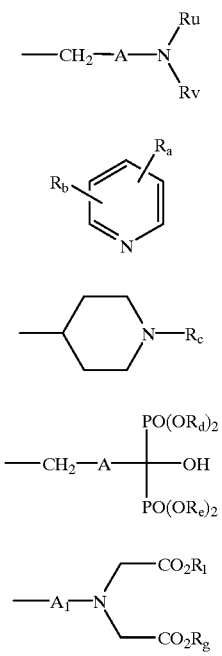

wherein A represents alkyl, suitably $C_{1-3}$ alkyl, $A_1$ is alkyl, suitably $C_{1-4}$ alky, and $R_a$, $R_b$, $R_c$, $R_d$ and $R_e$ each independently represent hydrogen, alkyl or aryl and $R_u$ and $R_v$ are as defined above.

As used herein, the term "alkenyl" includes straight or branched chain alkenyl groups having from 2 to 12, suitably 2 to 6 carbon and also includes such groups when forming part of other groups, an example is a butenyl group, such as a 2-butenyl group.

Suitable optional substituents for any alkenyl group includes the alkyl substituents mentioned above.

As used herein, the term "aryl" includes phenyl and naphthyl, especially phenyl.

Suitable optional substituents for any aryl group include up to 5 substituents, suitably up to 3 substituents, selected from alkyl, substituted alkyl, alkoxy, hydroxy, halogen, trifluoromethyl, acetyl, cyano, nitro, amino, mono-and di-alkylamino and alkylcarbonylamino Preferred optional substituents for any aryl group are selected from isobutyl, hydroxy, methoxy, phenoxy, diethylaminoethoxy, pyrrolidinoethoxy, carboxymethoxy, pyridyloxy, fluoro, chloro, amino, dimethylamino, aminomethyl, morpholino, bis(carbethoxy)hydroxymethyl, Suitable arylalkyl groups include aryl-$C_{1-3}$-alkyl groups such as phenylethyl and benzyl groups, especially benzyl.

Preferably, substituted aralkyl groups are substituted in the aryl moiety.

As used herein, the terms "heterocyclyl" or "heterocyclic" include saturated or unsaturated single or fused, including spiro, ring heterocyclic groups, each ring having 4 to 11 ring atoms, especially 5 to 8, preferably 5, 6 or 7 which ring atoms include 1, 2 or 3 heteroatoms selected from O, S, or N.

Suitable optional substituents for any heterocyclyl or heterocyclic group include up to 5 substituents, suitably up to 3 substituents, selected from alkyl, substituted alky, alkoxy, hydroxy, halo, amino, mono- or di-alkyl amino, alkoxycarbonyl, hydroxyalkyl, alkoxyalkyl, hydroxyalkoxyalkyl, alkoxyalkyloxyalkyl, aryl, aryloxy and heterocyclyl.

Preferred optional substituents for any heterocyclyl or heterocyclic group are selected from isobutyl, hydroxy, methoxy, phenoxy, diethylaminoethoxy, pyrrolidinoethoxy, carboxymethoxy, pyridyloxy, fluoro, chloro, amino, dimethylamino, aminomethyl, morpholino, bis(carbethoxy) hydroxymethyl.

For the avoidance of doubt a reference herein to "heterocylic" includes a reference to "heterocyclyl".

As used herein, the term "halo" includes fluoro, chloro and bromo, suitably fluoro and chloro, favourably chloro.

Certain of the carbon atoms of the compounds of formula (I)—such as those compounds wherein $R_1$–$R_8$ contains chiral alkyl chains are chiral carbon atoms and may therefore provide stereoisomers of the compound of formula (I). The invention extends to all stereoisomeric forms of the compounds of formula (I) including enantiomers and mixtures thereof, including racemates. The different stereoisomeric forms may be separated or resolved one from the other by conventional methods or any given isomer may be obtained by conventional stereospecific or asymmetric syntheses.

The compounds of formula (I) also possess two double bonds and hence can exist in one or more geometric isomers. The invention extends to all such isomeric forms of the compounds of formula (I) including mixtures thereof. The different isomeric forms may be separated one from the other by conventional methods or any given isomer may be obtained by conventional synthetic methods. Suitable salts of the compounds of the formula (I) are pharmaceutically acceptable salts.

Suitable pharmaceutically acceptable salts include acid addition salts and salts of carboxy groups.

Suitable pharmaceutically acceptable acid addition salts include salts with inorganic acids such, for example, as hydrochloric acid, hydrobromic acid, orthophosphoric acid or sulphuric acid, or with organic acids such, for example as methanesulphonic acid, toluenesulphonic acid, acetic acid, propionic acid, lactic acid, citric acid, fumaric acid, malic acid, succinic acid, salicylic acid, maleic acid or acetylsalicylic acid.

Suitable pharmaceutically acceptable salts of carboxy groups include metal salts, such as for example aluminium, alkali metal salts such as sodium or potassium and lithium, alkaline earth metal salts such as calcium or magnesium and ammonium or substituted ammonium salts, for example those with $C_{1-6}$ alkylamines such as triethylamine, hydroxy-$C_{1-6}$ alkylamines such as 2-hydroxyethylamine, bis-(2-hydroxyethyl)-amine or tri-(2-hydroxyethyl)-amine, cycloalkylamines such as dicyclohexylamine, or with procaine, 1,4-dibenzylpiperidine, N-benzyl-β-phenethylamine, dehydroabietylamine, N,N'-bisdehydroabietylamine, glucamine, N-methylglucamine or bases of the pyridine type such as pyridine, collidine or quinoline.

Suitable solvates of the compounds of the formula (I) are pharmaceutically acceptable solvates, such as hydrates.

The salts and/or solvates of the compounds of the formula (I) which are not pharmaceutically acceptable may be useful as intermediates in the preparation of pharmaceutically acceptable salts and/or solvates of compounds of formula (I) or the compounds of the formula (I) themselves, and as such form another aspect of the present invention.

A compound of formula (I) or a salt thereof or a solvate thereof, may be prepared: (a) for compounds of formula (I)

wherein Ra represents hydrogen, alkyl or optionally substituted aryl and $R_b$ represents a moiety of the above defined formula (a), by reacting a compound of formula (II):

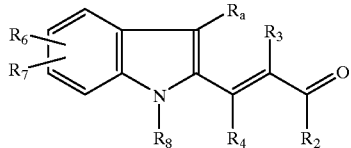
(II)

wherein $R_2$, $R_3$, $R_4$, $R_6$, $R_7$ and $R_8$ are as defined in relation to formula (I), with a reagent capable of converting a moiety of formula

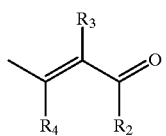

into a moiety of the above defined formula (a); or (b) for compounds of formula (I) where $R_a$ represents a moiety of the above defined formula (a) and $R_b$ represents hydrogen, alkyl or optionally substituted aryl, by treating a compound of formula (III):

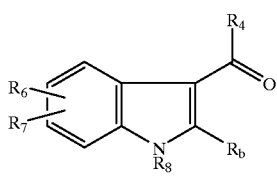
(III)

wherein $R_4$, $R_6$, $R_7$ and $R_8$ are as defined in relation to formula (I) with a compound of formula (IV):

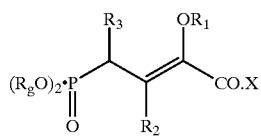
(IV)

wherein $R_1$, $R_2$, $R_3$ and X are as defined in relation to the compounds of formula (I) and $R_9$ is a $C_{1-4}$ alkyl group; and thereafter, as necessary, carrying out one or more of the following reactions:

(i) converting one compound of formula (I) into another compound of formula (I);

(ii) removing any protecting group;

(ii) preparing a salt or a solvate of the compound so formed.

In reaction (a) above, a suitable reagent capable of converting a moiety of the above defined formula

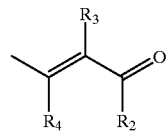

into a moiety of the above defined formula (a), includes conventional reagents used to convert C=O bonds into carbon carbon double bonds, such as Wittig or Horner-Emmons reagents, for example those of formula (V):

$$X_2-CH-CO-X_1$$
$$\quad\quad\; |$$
$$\quad\;\, OR_1$$
(V)

wherein $R_1$ is as defined in relation to the compounds of formula (I), $X_1$ represents X as defined in relation to formula (I) or a group convertible thereto and $X_2$ represents a moiety $(R_9O)_2P(O)-$ wherein $R_9$ is as defined above or a group $Ph_3P-$.

The reaction between the compounds of formula (II) and the reagent capable of converting the group of formula

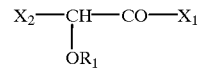

into the moiety of formula (a), may be carried out under the appropriate conventional conditions, depending upon the particular reagent chosen, for example:

When the reagent is a compound of formula (V) wherein $X_2$ is a moiety $(R_9O)_2P(O)-$, then the reaction is carried out under conventional Horner-Emmons conditions, using any suitable, aprotic solvent for example an aromatic hydrocarbon such as benzene, toluene or xylene, DMF, DMSO, chloroform, dioxane, dichloromethane, preferably, THF, acetonitrile, N-methylpyrrolidone, and the like or mixtures thereof, preferably an anhydrous solvent, at a temperature providing a suitable rate of formation of the required product, conveniently at ambient temperature or at an elevated temperature, such as a temperature in the range of from 30° C. to 120° C.; preferably the reaction is conducted in the presence of a base. Suitable bases for use in the last above mentioned reaction include organic bases, such as butyl lithium, lithium diisopropylamide (LDA), N,N-diisopropylethylamine, 1,5-diazabicyclo[4.3.0]-5-nonene (DBN), 1,5-diazabicyclo[5.4.0]-5-undecene (DBU), 1,5-diazabicyclo[2.2.2]octane (DABCO), and inorganic bases, such as sodium hydride; preferably sodium hydride, and generally the reaction is carried out in an inert atmosphere such as nitrogen.

When the reagent is a compound of formula (V) wherein $X_2$ is a moiety $Ph_3P-$, then the reaction is carried out under conventional Wittig conditions. Usually, the reaction is carried out in the presence of a base, in any suitable aprotic solvent. Suitable bases are organic bases such as triethylamine, trimethylamine, N,N-diisopropylethylamine (DIPEA), pyridine, N,N-dimethylaniline, N-methylmorpholine, 1,5-diazabicyclo[4.3.0]-5-nonene (DBN), 1,5-diazabicyclo[5.4.0]-5-undecene (DBU), 1,5-diazabicyclo[2.2.2]octane (DABCO) and inorganic bases such as sodium hydride, caesium carbonate, potassium carbonate, preferably sodium hydride. Suitable solvents are conventional solvents for use in this type of reaction, such as aromatic hydrocarbons such as benzene, toluene or xylene or the like; DMF, DMSO, chloroform, dioxane, dichloromethane, THF, ethyl acetate, acetonitrile, N-methylpyrrolidone or mixtures thereof, preferably dichloromethane. This reaction is carried out at any temperature providing a suitable rate of formation of the required product, conveniently at ambient temperature or at an elevated temperature, such as a temperature in the range of from −20° C. to 140° C., preferably in the range of from about room temperature to the reflux temperature of the solvent.

The reaction between the compounds of formula (III) and the Horner Emmons reagent of formula (IV) may be carried out under conventional Horner Emmons conditions such as those described above.

A compound of formula (II) may be prepared according to the reaction sequence shown in Scheme (I) below Scheme (I)

Error! Bookmark not defined.

wherein, subject to any qualification mentioned below, $R_2$, $R_3$, $R_4$, $R_5$, $R_6$, $R_7$ and $R_8$ are as defined in relation to the compounds of formula (I).

The reactions in Scheme (I) may be carried out using the appropriate conventional procedure, for example: when $R_2$=H, aldehyde (VII) can react with aliphatic aldehydes of formula (VI) in presence of bases such as sodium or potassium hydroxide affording compound (II). Alternatively, compounds of formula (II) may be prepared by the Wittig reaction of keto derivatives of formula (VIII) with the appropriate phosphonium salt (route A) using the reaction conditions which are known in the art and described, for example in "The Wittig Reaction", R. Adams Ed., Vol. 14, p. 270 (1965) or in *Angew. Chem. Int. Ed. Engl.*, 4, 645 (1965).

The reaction of compounds of formula (VII) with the above mentioned phosphonium salts are carried out in the presence of a base in any suitable solvent. Suitable bases include organic bases, such as triethylamine, trimethylamine, N,N-diisopropylethylamine (DIPEA), pyridine, N,N-dimethylaniline, N-methylmorpholine, 1,5-diazabicyclo[4.3.0]-5-nonene (DBN), 1,5-diazabicyclo[5.4.0]-5-undecene (DBU), 1,5-diazabicyclo[2.2.2]octane (DABCO) and inorganic bases, such as sodium hydride, caesium carbonate, potassium carbonate. Suitable solvents include conventionally used solvents, for example aromatic hydrocarbons such as benzene, toluene or xylene or the like; DMF, DMSO, chloroform, dioxane, dichloromethane, TBF, ethyl acetate, acetonitrile, N-methylpyrrolidone and the like or mixtures thereof. Preferably, the reaction is carried out at a reaction temperature of in the range of about −20° C. to 140° C., preferably about room temperature to the reflux temperature of the solvent.

When a compound of formula (VIII) is reacted with a substituted carbethoxymethylphosphorane (route B of Scheme (I)), the carboxylic ester obtained is then converted into the corresponding alcohol with a reducing agent, suitably a complex metal reducing agent such as lithium aluminium hydride (LiAlH$_4$), duisobutyl aluminium hydride (DIBAH) or lithium borohydride (LiBH$_4$), in any suitable aprotic solvent for example methylene dichloride, chloroform, dioxane, diethyl ether or THF, at any temperature providing a suitable rate of formation of the required product, such as a temperature in the range of from −30° C. to 60° C., for example at room temperature. Then, the intermediate alcohol is oxidised to aldehyde (II) with an oxidising agent such as manganese dioxide, periodinane (Dess-Martin reagent), pyridinium chlorochromate (PCC) or pyridinium dichromate (PDC) or a combination of oxalyl chloride and DMSO (Swern reaction), preferably manganese dioxide in methylene dichloride.

When $R_2$ is other than —H, e.g. alkyl, a compound of formula (II) is obtained directly from a compound of formula (VIII) by Wittig or Horner-Emmons reaction with the appropriate phosphorous ylides or phosphonates using conditions described above (route A of Scheme (I)).

When a compound of formula (VIII) is reacted with the above mentioned phosphonates using the Horner-Emmons reaction, the experimental conditions used are conventional conditions such as those reported, in *Tetrahedron Lett.* 1981, 461; *Can. J. Chem.*, 55, 562 (1977); *J. Am. Chem. Soc.*, 102, 1390 (1980); *J. Org. Chem.*, 44, 719 (1979); *Synthesis*, 1982, 391; and *Tetrahedron Lett.* 1982, 2183.

A compound of formula (IV) may be prepared according to the reaction sequence shown in Scheme (II) below.

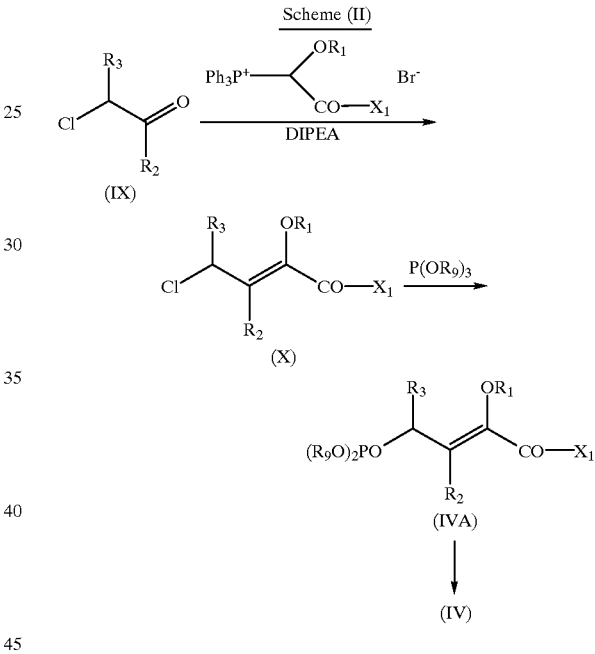

wherein, subject to any qualification mentioned below, $R_1$, $R_2$ and $R_3$ are as defined in relation to formula (I), $R_9$ is as defined in relation to formula (IV) and $X_1$ is as defined in relation to formula (V).

Compounds of formula (X) are prepared by reaction of, preferably anhydrous, chloroaldehydes or chloroketones of formula (IX) with suitable phosphonium compounds using the appropriate conventional procedure as described above for the Wittig reaction; conversion of intermediate compound (X) into the desired compound (IV) may be effected by reaction with a suitable trialkylphosphite $(R_9O)_3P$ wherein $R_9$ is as defined above, and the reaction is performed in any conventionally used solvent, preferably the trialkyl phosphite, and at a suitable reaction temperature, preferably at the boiling point of the solvent. For example from Scheme (III): the chloroacetaldehyde (IX) was treated with methyl 2-methoxy-2-(triphenylphosphonium)acetate bromide in the presence of DIPEA in chloroform and the intermediate (X) so obtained was converted into compound (IV) by refluxing in trimethyl phosphite.

The compounds of formula (V) can be prepared according to the reaction sequence shown in Scheme (III) below:

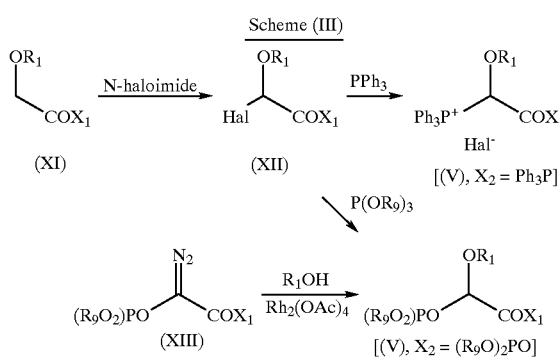

wherein, subject to any qualification mentioned below, $R_1$ and $R_9$ are as defined in relation to formula (I) and $X_1$ is as defined in relation to formula (V).

The starting material is an (α-alkoxycarboxylic ester of formula (XI) which is commercially available or which is prepared according to the methods known in the art, for example those reported in *Rodd's Chemistry of Organic Compounds, Vol ID,* p. 96 (1965), S. Coffey Ed., Elseviers. The compound of formula (XI) is reacted with an N-haloimide, for example N-bromosuccinimide in the presence of a radical producing agent such as azobisisobutyronitrile or benzoyl peroxide in a suitable solvent such as carbon tetrachloride, benzene, for example carbon tetrachloride and at a reaction temperature in the range of from −30° C. and 80° C., for example at room temperature; examples of such a reaction may be found in the literature, for example *J. Org. Chem.,* 41, 2846 (1976). The halocompound obtained, of formula (XII), is then reacted either with triphenylphosphine or with a trialkyl phosphite $P(OR_9)_3$ to give the required compound of formula (V) as shown in scheme (III).

When the compound of formula (XII) is reacted with triphenylphosphine, the reaction is performed in any conventionally used solvent, for example dioxane, tetrahydrofuran, , benzene, xylene or, preferably, toluene at a suitable reaction temperature in the range of from −30° C. to 80° C., for example at room temperature (examples of this conversion are reported in the literature, for example in *Chem. Ber.,* 97, 1713 (1964)).

When the compound of formula (XII) is reacted with trialkyl phosphite $P(OR_9)_3$, the reaction is performed in any conventionally used solvent, preferably the trialkyl phosphite, and at a suitable reaction temperature, preferably at the boiling point of the solvent (examples of this conversion are reported in the literature, for example in *Liebigs Ann. Chem.,* 699, 53 (1966).

Alternatively, a compound of formula (V) in which $R_2$ is $(R_9O)_2PO$ may be prepared using the procedure depicted in Scheme (III), by reacting a diazophosphonoacetates of formula (XII) with an alcohol or phenol of formula $R_1OH$, wherein $R_1$ is as defined in relation to formula (I), in the presence of rhodium (II) acetate as described in the literature, for example in *Tetrahedron,* 50, 3177 (1994) or in *Tetrahedron,* 48, 3991 (1992).

The compounds of formula (III), (VII) and (VIII), are known compounds or they are prepared using methods analogous to those used to prepare known compounds, such as those described in *J. Org. Chem.,* 47, 757 (1982); *Heterocycles,* 22, 1211 (1984); *Tetrahedron,* 44, 443 (1988).

The compounds of formula (VI), (IX) and (XI) are known compounds or they are prepared using methods analogous to those used to prepare known compounds, such as those described in J. March, *Advanced Organic Chemistry,* 3rd Edition (1985), Wiley Interscience.

Suitable conversions of one compound of formula (I) into another compound of formula (I) includes converting a compound of formula (I) wherein X represents a hydroxy group or an alkoxy group into a compound of formula (I) wherein X represents a different alkoxy group or a moiety of the above defined formula $NR_sR_t$. Such conversions are shown below in Scheme (IV):

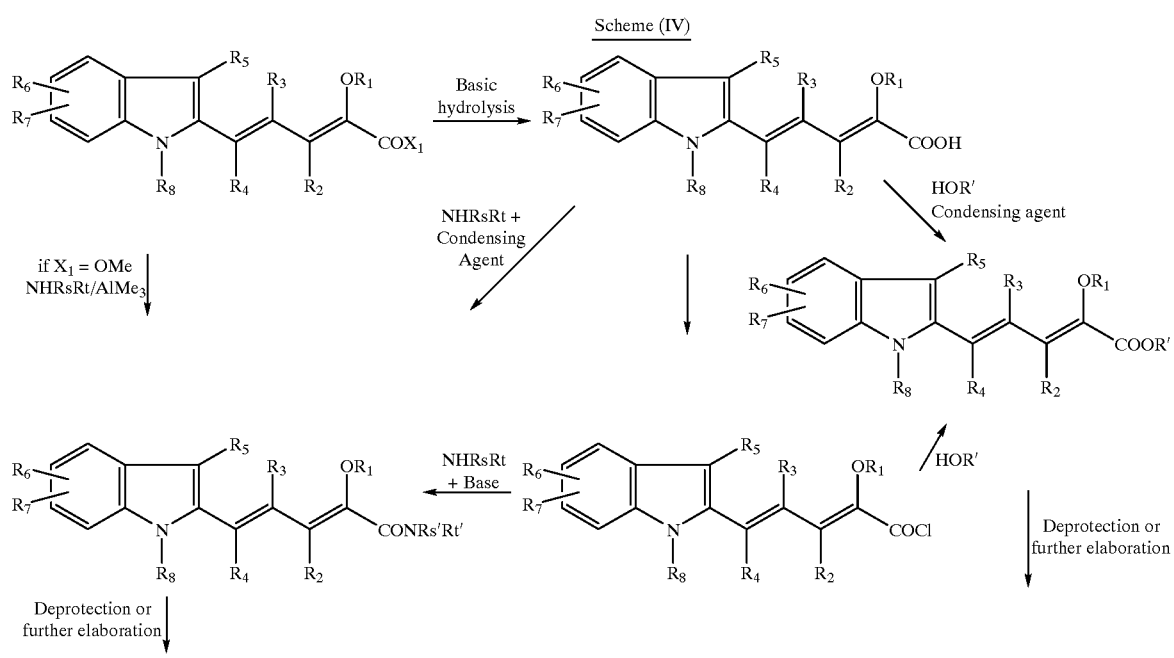

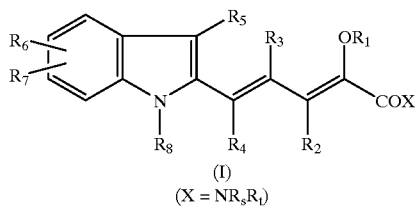

(I)
(X = NR$_s$R$_t$)

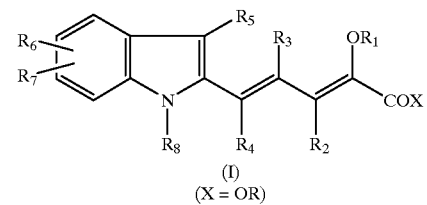

(I)
(X = OR)

wherein, subject to any qualification mentioned below, R$_2$, R$_3$, R$_4$, R$_5$, R$_6$, R$_7$, R$_8$ and X are as defined in relation to the compounds of formula (I), R$_s$' is R$_s$ or a protected form thereof, R$_t$' is R$_t$ or a protected form thereof and R' is X when X is an alkoxy group.

The conversion of one compound of formula (I) into another compound of formula (I) may be carried out using the appropriate conventional procedure; for example, the above mentioned conversion of a compound wherein X represents a hydroxy group or an alkoxy group into a compound wherein X represents a moiety of the above defined formula NR$_s$R$_t$ or another alkoxy group may be carried out as follows:

(i) when X is alkoxy, by basic hydrolysis, using for example potassium hydroxide, to provide a compound of formula (I) wherein X is hydroxy, and thereafter(a) for preparing compounds wherein X represents a moiety of the above defined formula NR$_s$R$_t$, treating with a compound of formula HNR$_s$'R$_t$' wherein R$_s$' and R$_t$' are as defined above or (b) for preparing compounds of formula (I) wherein X represents alkoxy, by treating with a compound of formula R'OH wherein R' is the required alkoxy group; and thereafter optionally deprotecting; or (ii) when X is hydroxy, by using analogous procedures to those mentioned above in (I).

Preferably the reaction with the compounds of formula HNR$_s$'R$_t$' or with compounds of formula R'OH takes place after activation of the carboxylic group.

A carboxyl group may be activated in conventional manner, for example, by conversion into an acid anhydride, acid halide, acid azide or an activated ester such as cyanomethyl ester, thiophenyl ester, p-nitrophenyl ester, p-nityrothiophenyl ester, 2,4,6-trichlorophenyl ester, pentachlorophenyl ester, pentafluorophenyl ester, N-hydroxyphthalimido ester, 8-hydroxypiperidine ester, N-hydroxysuccinimide ester, N-hydroxybenzotriazole ester, or the carboxyl group may be activated using a carbodiimide such as N,N'-dicyclohexylcarbodiimide (DCC) or 1-ethyl-3-[3-(dimethylamino)propyl]carbodiimide hydrochloride (WSC), either in the presence or the absence of hydroxybenzotriazole (HOBt) or 1-hydroxy-7-azabenzotriazole (HOAt); or it may be activated using N,N'-carbonyldiimidazole, Woodward-K reagent, Castro's reagent or an isoxazolium salt.

Condensation of an activated carboxyl group with an amino group or with an alcoholic group may be carried out in the presence of a base, in any suitable solvent.: Suitable bases include organic bases, such as triethylamine, trimethylamine, N,N-diisopropylethylamine (DIPEA), pyridine, N,N-dimethylaniline, 4-dimethylaminopyridine (DMAP), N-methylmorpholine, 1,5-diazabicyclo[4.3.0]-5-nonene (DBN), 1,5-diazabicyclo[5.4.0]-5-undecene (DBU), 1,5-diazabicyclo[2.2.2]octane (DABCO), and inorganic bases, such as potassium carbonate. Suitable solvents include conventionally used solvents, for example DMF, dimethyl sulfoxide (DMSO), pyridine, chloroform, dioxane, dichloromethane, THF, ethyl acetate, acetonitrile, N-methylpyrrolidone and hexamethylphosphoric triamide and mixtures thereof. The reaction temperature may be within the usual temperature range employed in this type of condensation reaction, and generally in the range of about −40° C. to about 60° C., preferably from about −20° C. to about 40° C.

When the reaction is carried out in the presence of a suitable condensing agent, for example a carbodiimide, N,N'-carbonyldiimidazole, Woodward-K reagent, Castro's reagent or the like, the condensing agent is preferably employed in an amount from equimolar to about 5 times the molar quantity of the starting material and the reaction is performed in a suitable solvent for example a halogenated hydrocarbon such as dichloromethane, chloroform, carbon tetrachloride, tetrachloroethane or the like; an ether such as dioxane, ThF, dimethoxyethane or the like, a ketone such as acetone, methyl ethyl ketone or the like; acetonitrile, ethyl acetate, DMF, dimethylacetamide, DMSO or the like. Preferably the condensation is carried out in an anhydrous solvent, and at a reaction temperature in the range of from about −10° C. to 60° C., preferably about 0° C. to room temperature.

Alternatively, conversion of one compound of formula (I) in which X is O-alkyl into another compound of formula (I) in which X is NR$_s$R$_t$ may be effected by treating the said compound of formula (I) directly with a compound of formula HNR$_s$'R$_t$' in the presence of a trialkylaluminium reagent such as trimethylaluminium or triethylaluminium, according to known procedures, such as those disclosed in *Tetrahedron Lett.*, 48, 4171 (1977); and, if necessary, deprotecting or converting the compound of formula (I) in which X is NR$_s$'R$_t$' into a compound of formula (I) in which X is NR$_s$R$_t$.

The trialkylaluminium reagent is generally employed in the above mentioned reactions in an amount of from equimolar to about 5 times the molar quantity of the starting material, preferably 2–3 times the molar quantity of the starting material and the reaction is performed in a suitable solvent for example a halogenated hydrocarbon such as dichloromethane, chloroform, carbon tetrachloride, tetrachloroethane or the like; an ether such as dioxane, THF, dimethoxyethane or the like. Preferably the condensation is carried out in an anhydrous solvent, and at a reaction temperature of about, generally −20° C. to 120° C., preferably about 0° C. to the reflux temperature of the solvent.

Amines of general formula HNR$_s$R$_t$ may be prepared using the methods known in the art for the preparation of amines, for example as taught in *Houben-Weil, Methoden der Organischen Chemie,* Vol. XI/1(1957) and Vol. E16d/2 (1992), Georg Thieme Verlag, Stuttgart.

In particular, amines of the general formula HNR$_s$R$_t$ wherein one of R$_S$ and R$_t$ represents hydrogen and the other represents a moiety (a), (b), (c), (d) (e) as defined above or a particular example thereof, are prepared according to the methods summarised in Scheme (V) below:

SCHEME (V)

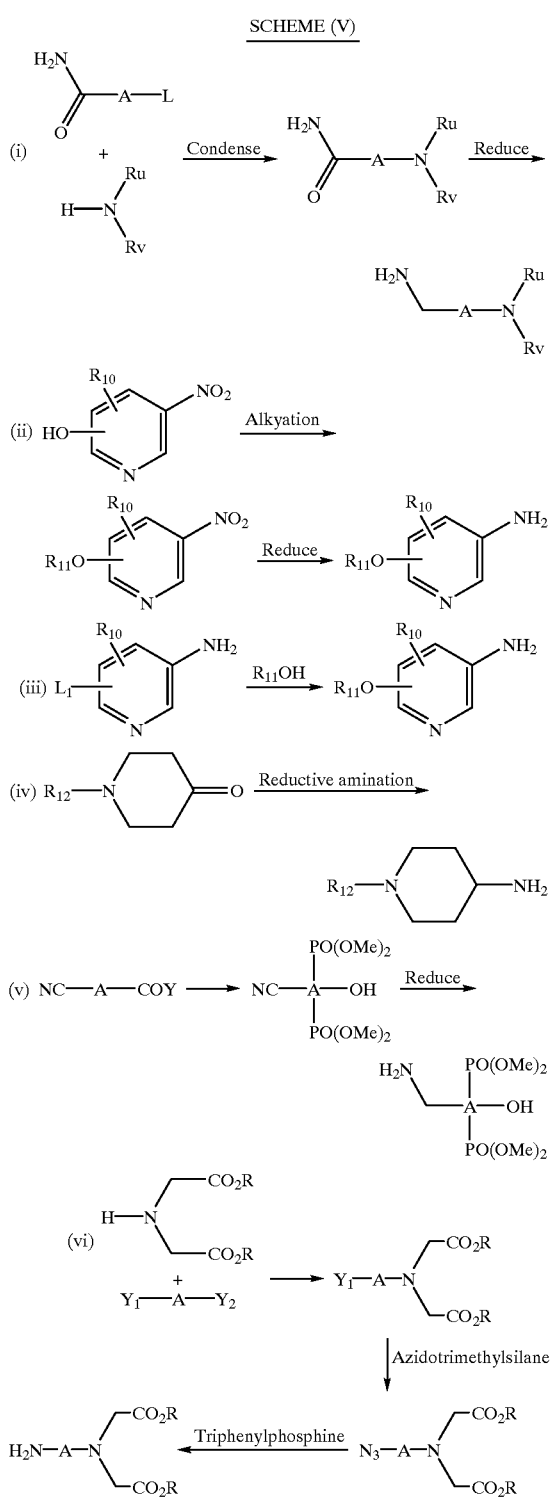

wherein R an alkyl or aryl group, $R_u$ and $R_v$ are as defined above, A is a bond or an alkyl chain, $R_{10}$ is hydrogen (in ii) or halogen (in (iii)) and $R_{11}$ is an alkyl group, $R_{12}$ is alkyl or aryl, L and $L_1$ are leaving groups, for example halogen or mesylate, Y is halogen, $Y_1$ is a leaving group, for example a halogen and and $Y_1$ and $Y_2$ are leaving groups such as halogens, for example $Y_1$ is chloride and $Y_2$ is bromine.

With regard to Scheme (V):

The reduction of the amide function in (i) is suitably carried out using known methods, for example by using mixed hydride reducing agents, such as lithium aluminium hydride and methods described in *Org Synth* Coll Vol 4 564.

The reduction of the nitropyridine in (ii) is suitably carried out using the method described in *J. Org. Chem.* 58, 4742 (1993).

The alkylation of the hydroxy-nitropyridine in (ii) may be effected by using the method described in *J. Org. Chem* 55, 2964 (1990).

The displacement reaction in (iii) is suitably carried out using the method described in *Helvetica Chemica Acta* 47 (2), 45 (1964)

The reductive amination of the ketone in (iv) can be performed with benzylamine to give an imine intermediate which is then reduced using known methods and reducing agents such as sodium borohydride or lithium aluminium hydride. Debenzylation can then be performed again using conventional methods, for example with hydrogen in the presence of a catalyst such as palladium on charcoal.

The reduction of the nitrile in (v) is suitably carried by catalytic hydrogenation over platinium oxide.

The reaction of acid halide NC-A-COY to provide the dialkylphosphonate in (v) is effected by following the procedure described in *J Org Chem* 36, 3843 (1971).

The reaction of the azide with triphenylphosphine in (vi) is carried out in wet tetrahydrofuran as described in *Bull Soc Chim Fr* 1985, 815.

The azides in (vi) are prepared as shown using azidotrimethylsilane, following the procedure described in *Synthesis* 1995, 376.

The reaction of compound $Y_1$-A-$Y_2$ and the amine derivative in (vi) proceeds under conventional displacement reaction conditions.

The substrates in the above reactions (i), (ii), (iii), (iv), (v) and (vi) are known commercially available compounds.

A compound of formula (I) or a solvate thereof may be isolated from the above mentioned processes according to standard chemical procedures.

The preparation of salts and/or solvates of the compounds of formula (I) may be performed using the appropriate conventional procedure.

If required mixtures of isomers of the compounds of the invention may be separated into individual stereoisomers and diastereoisomers by conventional means, for example by the use of an optically active acid as a resolving agent. Suitable optically active acids which may be used as resolving agents are described in "*Topics in Stereochemistry*", Vol. 6, Wiley Interscience, 1971, Allinger, N. L. and Eliel, W. L. Eds.

Alternatively, any enantiomer of a compound of the invention may be obtained by stereospecific synthesis using optically pure starting materials of known configuration.

The absolute configuration of compounds may be determined by conventional methods such as X-ray crystallographic techniques.

The protection of any reactive group or atom, may be carried out at any appropriate stage in the aforementioned processes. Suitable protecting groups include those used conventionally in the art for the particular group or atom being protected. Protecting groups may be prepared and removed using the appropriate conventional procedure, for example OH groups, including diols, may be protected as the silylated derivatives by treatment with an appropriate silylating agent such as di-tert-butylsilylbis (trifluoromethanesulfonate): the silyl group may then be removed using conventional procedures such as treatment with hydrogen fluoride, preferably in the form of a pyridine complex and optionally in the presence of alumina, or by treatment with acetyl chloride in methanol. Alternatively benzyloxy groups may be used to protect phenolic groups, the benzyloxy group may be removed using catalytic hydrogenolysis using such catalysts as palladium (II) chloride or 10% palladium on carbon.

Amino groups may be protected using any conventional protecting group, for example tert-butyl esters of carbamic acid may be formed by treating the amino group with di-tert-butyldicarbonate, the amino group being regenerated by hydrolysing the ester under acidic conditions, using for example hydrogen chloride in ethyl acetate or trifluoroacetic acid in methylene dichloride. An amino group may be protected as a benzyl derivative, prepared from the appropriate amine and a benzyl halide under basic conditions, the benzyl group being removed by catalytic hydrogenolysis, using for example a palladium on carbon catalyst.

Indole NH groups and the like may be protected using any conventional group, for example benzenesulphonyl, methylsulphonyl, tosyl, formyl, acetyl (all of them removable by treatment with alkaline reagents), benzyl (removable either with sodium in liquid ammonia or with $AlCl_3$ in toluene), allyl (removable by treatment with rhodium (III) chloride under acidic conditions), benzyloxycarbonyl (removable either by catalytic hydrogenation or by alkaline treatment), trifluoroacetyl (removable by either alkaline or acidic treatment), t-butyldimethylsilyl (removable by treatment with tetrabutylammonium fluoride), 2-(trimethylsilyl) ethoxymethyl (SEM) (removable by treatment with tetrabutylammonium fluoride in the presence of ethylendiamine), methoxymethyl (MOM) or methoxyethyl (MEM) groups (removed by mild acidic treatment).

Carboxyl groups may be protected as alkyl esters, for example methyl esters, which esters may be prepared and removed using conventional procedures, one convenient method for converting carbomethoxy to carboxyl is to use aqueous lithium hydroxide.

A leaving group or atom is any group or atom that will, under the reaction conditions, cleave from the starting material, thus promoting reaction at a specified site. Suitable examples of such groups unless otherwise specified are halogen atoms, mesyloxy, p-nitrobenzensulphonyloxy and tosyloxy groups.

The salts, esters, amides and solvates of the compounds mentioned herein may as required be produced by methods conventional in the art: for example, acid addition salts may be prepared by treating a compound of formula (I) with the appropriate acid.

Esters of carboxylic acids may be prepared by conventional esterification procedures, for example alkyl esters may be prepared by treating the required carboxylic acid with the appropriate alkanol, generally under acidic conditions.

Amides may be prepared using conventional amidation procedures, for example amides of formula $CONR_sR_t$ may be prepared by treating the relevant carboxylic acid with an amine of formula $HN R_s R_t$ wherein $R_s$ and $R_t$ are as defined above. Alternatively, a $C_{1-6}$ alkyl ester such as a methyl ester of the acid may be treated with an amine of the above defined formula $HNR_sR_t$ to provide the required amide.

As mentioned above the compounds of the invention are indicated as having useful therapeutic properties:

The present invention accordingly provides a compound of formula (I), or a pharmaceutically acceptable solvate thereof, for use as an active therapeutic substance.

In particular the present invention provides a compound of formula (I) or a pharmaceutically acceptable salt thereof and/or a pharmaceutically acceptable solvate thereof, for use in the treatment of and/or prophylaxis of osteoporosis and related osteopenic diseases.

The present invention also provides a compound of formula (I) or a pharmaceutically acceptable salt thereof and/or a pharmaceutically acceptable solvate thereof, for use in the treatment of tumours, especially those related to renal cancer, melanoma, colon cancer, lung cancer and leukemia, viral conditions (for example those involving Semliki Forest virus, Vesicular Stomatitis virus, Newcastle Disease virus, Influenza A and B viruses, HIV virus), ulcers (for example chronic gastritis and peptic ulcer induced by Helicobacter pylori), for use as immunosupressant agents in autoimmune diseases and transplantation, antilipidemic agents for the treatment and/or prevention of hypercholesterolemic and atherosclerotic diseases and to be useful for the treatment of AIDS and Alzheimer's disease. These compounds are also considered useful in treating angiogenic diseases, i.e. those pathological conditions which are dependent on angiogenesis, such as rheumatoid arthritis, diabetic retinopathy, psoriasis and solid tumours.

A compound of formula (I), or a pharmaceutically acceptable salt thereof and/or a pharmaceutically acceptable solvate thereof, may be administered per se or, preferably, as a pharmaceutical composition also comprising a pharmaceutically acceptable carrier.

Accordingly, the present invention also provides a pharmaceutical composition comprising a compound of formula (I), or a pharmaceutically acceptable salt thereof, or a pharmaceutically acceptable solvate thereof, and a pharmaceutically acceptable carrier thereof.

Active compounds or a pharmaceutically acceptable salt thereof and/or a pharmaceutically acceptable solvate thereof is normally administered in unit dosage form.

An amount effective to treat the disorders hereinbefore described depends upon such factors as the efficacy of the active compounds, the particular nature of the pharmaceutically acceptable salt or pharmaceutically acceptable solvate chosen, the nature and severity of the disorders being treated and the weight of the mammal. However, a unit dose will normally contain 0.01 to 50 mg, for example 1 to 25 mg, of the compound of the invention. Unit doses will normally be administered once or more than once a day, for example 1, 2, 3, 4, 5 or 6 times a day, more usually 1 to 3 or 2 to 4 times a day such that the total daily dose is normally in the range, for a 70 kg adult of 0.01 to 250 mg, more usually 1 to 100 mg, for example 5 to 70 mg, that is in the range of approximately 0.0001 to 3.5 mg/kg/day, more usually 0.01 to 1.5 mg/kg/day, for example 0.05 to 0.7 mg/kg/day.

At the above described dosage range, no toxicological effects are indicated for the compounds of the invention.

The present invention further provides a method for the treatment of osteoporosis and related osteopenic diseases in a human or non-human mammal, which comprises administering an effective, non-toxic, amount of a compound of formula (I) or a pharmaceutically acceptable solvate thereof, to a human or non-human mammal in need thereof.

The present invention also provides a method for the treatment of tumours, especially those related to renal cancer, melanoma, colon cancer, lung cancer and leukemia, viral conditions (for example those involving Semliki Forest, Vesicular Stomatitis, Newcastle Disease, Influenza A and B, HIV viruses), ulcers (for example chronic gastritis and peptic ulcer induced by *Helicobacter pylori*), autoimmune diseases and transplantation, for the treatment and/or prevention of hypercholesterolemic and atherosclerotic diseases, AIDS and Alzheimer's disease, angiogenic diseases, such as rheumatoid arthritis, diabetic retinopathy, psoriasis and solid tumours, in a human or non-human mammal, which comprises administering an effective, non-toxic, amount of a compound of formula (I) or a pharmaceutically acceptable solvate thereof, to a human or non-human mammal in need thereof.

In such treatments the active compound may be administered by any suitable route, e.g. by the oral, parenteral or topical routes. For such use, the compound will normally be employed in the form of a pharmaceutical composition in association with a human or veterinary pharmaceutical carrier, diluent and/or excipient, although the exact form of the composition will naturally depend on the mode of administration.

Compositions are prepared by admixture and are suitably adapted for oral, parenteral or topical administration, and as such may be in the form of tablets, capsules, oral liquid preparations, powders, granules, lozenges, pastilles, reconstitutable powders, injectable and infusable solutions or suspensions, suppositories and transdermal devices. OCrally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

These solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the active compound.

For topical administration, the composition may be in the form of a transdermal ointment or patch for systemic delivery of the active compound and may be prepared in a conventional manner, for example, as described in the standard textbooks such as 'Dermatological Formulations'—B. W. Barry (Drugs and the Pharmaceutical Sciences—Dekker) or Harrys Cosmeticology (Leonard Hill Books).

The present invention also provides the use of a compound of formula (I), or a pharmaceutically acceptable salt thereof, or a pharmaceutically acceptable solvate thereof, for the manufacture of a medicament for the treatment of osteoporosis and related osteopenic diseases.

The present invention also provides the use of a compound of formula (I), or a pharmaceutically acceptable salt thereof, or a pharmaceutically acceptable solvate thereof, for the manufacture of a medicament for the treatment of tumours, especially those related to renal cancer, melanoma, colon cancer, lung cancer and leukemia., viral conditions (for example those involving Semliki Forest, Vesicular Stomatitis, Newcastle Disease, Influenza A and B, HIV viruses), ulcers (for example chronic gastritis and peptic ulcer induced by Helicobacter pylori), autoimmune diseases and transplantation, for the treatment and/or prevention of hypercholesterolemic and atherosclerotic diseases, AIDS and Alzheimer's disease, angiogenic diseases, such as rheumatoid arthritis, diabetic retinopathy, psoriasis and solid tumours,.

No unacceptable toxicological effects are expected with compounds of the invention when administered in accordance with the invention. As is common practice, the compositions will usually be accompanied by written or printed directions for use in the medical treatment concerned.

The following, descriptions, examples and pharmacological methods illustrate the invention but do not limit it in any way.

Preparation 1

Indole-2-carboxaldehyde. To an ice cold solution of LiAl$_4$ (2.56 g, 67.5 mmol) in anhydrous TIF (150 ml) under nitrogen, ethyl indole-2-carboxylate (9 g, 47 mmol) (*Heterocycles*, 1984, 22, 1211) dissolved in dry THF (70 ml) was added dropwise. The mixture was stirred for 45 min at 0° C. and then quenched by the sequential addition of water (2.5 ml), 15% aqueous NaOH (2.5 ml) and water (7.5 ml). The mixture was filtered through a Celite pad and then washed with THF (2×75 ml). The filtrate dried over Na$_2$SO$_4$ and evaporated in vacuo yielded 8.62 g of a colourless oil. This was dissolved in dichloromethane (200 ml), and activated manganese dioxide (20 g, 0.23 mol) was added. The mixture was stirred at room temperature for 12 h and then filtered through a Celite pad which was washed with warm acetone (4×100 ml), and the combined filtrates were evaporated to dryness, yielding 6.72 g (98.5%) of the title compound, m.p.=134–137° C.

Preparation 2

(E)-3-(2-Indolyl)-2-propenaldehyde. Indole 2-carboxaldehyde (6.72 g, 46.3 mmol) was dissolved in dry toluene (450 ml) and treated with (formylmethylene) triphenylphosphorane (21.3 g, 70 mmol). The reaction mixture was treated under reflux for 4 h, allowed to cool and chromatographed over silica gel using toluene (2×500 ml) and then hexane/EtOAc (3:1) (2×500 ml) as the eluent. Evaporation of the solvent and recrystallization of the residue from toluene yielded 4.96 g (62.6%) of the title compound, m.p.=203–204° C.

Preparation 3

(E)-3-(5-Methoxy-2-indolyl)-2-propenaldehyde. 5-Methoxyindole-2-carboxaldehyde (1.5 g, 8.5 mmol) was dissolved in dry toluene (30 ml) and treated with (formylmethylene)triphenylphosphorane (3 g, 9.8 mmol). The reaction mixture was stirred at 85° C. for 5 h, allowed to cool and chromatographed over silica gel using hexane/EtOAc (7:3). Evaporation of the solvent yielded 0.45 g (26 %) of (E)-3-(5-methoxy-2-indolyl)-2-propenaldehyde, m.p.=145–147° C.

Preparation 4

(E)-2-Ethyl-3-(2-indolyl)-2-propenaldehyde. To a solution of KOH pellets (0.4 g, 7.1 mmol) in $H_2O$ (5 ml), indole-2-carboxaldehyde (0.5 g, 3.44 mmol) in EtOH (45 ml) was added. After cooling to 0° C. butyraldehyde (0.31 ml, 3.44 mmol) was added and the reaction mixture was stirred at room temperature for 12 h. The ethanol was removed under vacuum and the aqueous solution was adjusted to pH 5 and extracted with EtOAc (3×10 ml). The combined organic layers were washed with brine (10 ml), dried over $Na_2SO_4$ and evaporated under vacuum. The residue was purified by flash-chromatography (hexane/EtOAc 7:3) to afford, after trituration with isopropyl ether, 0.3 g (44%) of the title compound.

Preparation 5

A) Ethyl (2E)-3-[2-(3-methylindolyl)]-3-phenyl-2-propenoate. A mixture of 2-benzoyl-3-methylindole (*J. Org. Chem.*, 37, 3622 (1972)) (0.6 g, 2.55 mmol) and (carbethoxymethylene) triphenylphosphorane (2.1 g, 6 mmol) was heated at 150° C. in a sealed tube for 40 h. After cooling, the residue was chromatographed over silica gel (EtOAc/hexane 2:8) obtaining 0.2 g (25.7%) of the crude title compound as a solid, m.p.=125–130° C.

B) (2E)-3-[2-(3-Methylindolyl)]-3-phenyl-2-propenaldehyde. The crude ethyl (2E)-3-[2-(3-methylindolyl)]-3-phenyl-2-propenoate (0.2 g, 0.65 mmol) was dissolved in dichloromethane (10 ml) and 1M solution of DIBAH in hexane (2.5 ml, 2.5 mmol) was added dropwise, under nitrogen atmosphere, at 0° C. Stirring was continued for 30 minutes, then the temperature was allowed to reach room temperature and a saturated solution of $NH_4Cl$ (10 ml) was added. The resulting mixture was filtered on a Celite pad. The phases were separated and the organic layer was washed with water, dried over $Na_2SO_4$ and the solvent evaporated under vacuum to give the crude intermediate alcohol (0.12 g) as an oil. This was dissolved in dichloromethane (5 ml) and 85% activated $MnO_2$ (0.3 g, 2.93 mmol) was added. The mixture was stirred at room temperature for 3 hours, and filtered on a Celite pad. The filtrate was evaporated under reduced pressure to yield 0.09 g (53%) of the title compound as a yellow oil.

Preparation 6

Methyl (Z)-4-chloro-2-methoxy-2-butenoate. A mixture of 63.5 g of chloroacetaldehyde (as a 50–55% water solution) and 450 ml of $CHCl_3$ was heated to reflux and then 300 ml of azeotrope ($H_2O$—$CHCl_3$) were collected. This operation was repeated twice, then the residual 300 ml were dried over $Na_2SO_4$ and filtered, obtaining a clear orange solution, to which methyl 2-methoxy-2-(triphenylphosphonium)acetate bromide (30 g, 67.3 mmol) was added. Stirring was continued at room temperature while diisopropylethylamine (13 ml, 74.6 mmol) was added dropwise. The internal temperature rose to 50° C. After two hours the solvent was removed under vacuum and the residue was taken-up in diethyl ether (500 ml), washed with 1N HCl and then with $H_2O$. The organic phase was dried over $Na_2SO_4$ and the solvent evaporated. The residue was distilled at reduced pressure (56–60° C., 1 mbar) to afford 9.56 g (86%) of the title compound.

Preparation 7

Trimethyl (Z)-2-methoxyphosphono-2-butenoate. A mixture of methyl (Z)-4chloro-2-methoxy-2-butenoate (9.50 g, 58 mmol) and 1 g of potassium iodide was stirred at room temperature. Trimethyl phosphite (10 ml, 85 mmol) was added dropwise, while the internal temperature rose to 80° C. The mixture was then heated to reflux for 4 hours. Distillation at reduced pressure (0.1 mbar, 200–210° C.) yielded 8.2 g (60%) of the title compound.

Preparation 8

A) Ethyl α-oxo-3-(2-nitro-4,5-dichlorophenyl) propanoate. To a suspension of potassium (24.5 g, 0.626 g.a.) in anhydrous diethyl ether (245 ml), a solution of absolute ethanol (158 ml) and anhydrous diethyl ether (126 ml) was added dropwise under nitrogen during a period of four hours. The resulting solution was diluted with diethyl ether (600 ml) and then diethyl oxalate (85.5 ml, 630 mmol) was added dropwise in about 30 min. To the resulting yellow mixture, a solution of 3-nitro-4,5-dichlorotoluene (130 g, 630 mmol) in anhydrous diethyl ether (225 ml) was added dropwise in 1 hour at room temperature. Stirring was continued for additional three hours and the dark-brown mixture was settled at room temperature for two days. The potassium salt was collected by filtration, washed with anhydrous diethyl ether (200 ml) and dried to give 210 g of a dark-brown powder. The solid was suspended in a mixture of water (200 ml) and ethyl acetate (400 ml) and then acidified with 10% HCl. The organic layer was washed with brine, dried over $Na_2SO_4$ and evaporated under vacuum to obtain 115.1 g (60.1%) of the title compound as a light brown solid, m.p.=92–94° C.

B) Ethyl 5,6-dichloroindole-2-carboxylate A mixture of ethyl α-oxo-3-(2-nitro-4,5-dichlorophenyl)propanoate (20 g, 65.3 mmol) and iron powder (32 g) in ethanol (125 ml) and acetic acid (125 ml) was refluxed for two hours. After cooling, the resulting mixture was evaporated under vacuum and the solid residue was dissolved in THF (200 ml) and chromatographed on Florisil (100 g) eluting with THF (1000 ml). Evaporation of the collected fractions gave 15.5 g (92%) of the title compound as a light brown powder, m.p. 215°–218° C.

C) 5,6-Dichloroindole-2-carboxaldehyde was obtained from ethyl 5,6dichloroindole-2-carboxylate according to the preparation 1. Yield (65.4 %), mp=207–208°

D) (E) Ethyl 3-(5,6-dichloro-2-indolyl)-2-propenoate. Fourteen grams of ethyl 5,6-dichloroindole-2-carboxaldehyde (65.4 mmol) was dissolved under nitrogen in 650 ml of toluene and heated at 90° C. with 22.28 g of (ethoxycarbonylmethylene)triphenylphosphorane (65.4 mmol). After 40 min the reaction was completed. The solvent was evaporated under reduced pressure and the reaction mixture was purified by flash-chromatography (Hexane/AcOEt, 8:2) obtaining 16.23 g of the title compound.

E) (E) 3-(5,6-Dichloro-2-indolyl)-2-propen-1-ol. To a solution of 16.23 g of (E) ethyl 3-(5,6-dichloro-2-indolyl)-2-propenoate (57.12 mmol) in 300 ml of THF, under nitrogen, 114 ml of DIBAL (1M solution in hexane, 2 eq) were added dropwise at −20° C. The reaction mixture was maintained at this temperature for 1 h and then quenched with $H_2O$. The mixture was allowed to rise to room temperature, diluted with diethyl ether (200 ml) and filtered on a Celite pad, washing with 300 ml of diethyl ether. The dark-red solution was dried over $MgSO_4$ and evaporated under vacuum to give 13.8 g (100%) of the title compound.

F) (E) 3-(5,6-Dichloro-2-indolyl)-2-propenaldehyde. To a solution of 13.8 g of (E) 3-(5,6-dichloro-2-indolyl)-2-propen-1-ol (57.12 mmol) in 450 ml of diethyl ether, 35 g of MnO2 and 35 g of NaCl were added. The reaction mixture was stirred for two days at room temperature, filtered on a Celite pad, washed with $Et_2O$ and dried over $MgSO_4$ to afford 11.5 g (83.8%) of the title compound.

Preparation 9

A) 1-(3-Chloropropionyl)morpholine. To an ice-cold, stirred solution of morpholine (5 g, 0.057 mol) and triethylamine (8 ml, 0.057 mol) in $CH_2Cl_2$ (5 ml) a solution of 3-chloropropionyl chloride (5.5 ml, 0.057 mol) in $CH_2Cl_2$ (15 ml) was added dropwise, and stirring was continued at room temperature for 12 hours. The solvent was removed under vacuum and the residue was dissolved in AcOEt (15 ml). The organic layer was washed with 10% HCl (10 ml), saturated solution of sodium bicarbonate (10 ml) and brine (10 ml), dried over $Na_2SO_4$ and evaporated under vacuum to obtain 9.61 g (94%) of the title compound.

B) 1-[3-[(4-Hydroxybutyl)amino]propionyl]morpholine. A mixture of 1-(3-chloropropionyl)morpholine (1 g, 5.63 mmol), 4-amino-1-butanol (1 ml, 11.26 mmol) and potassium carbonate (1.94 g, 14.07 mmol) in acetonitrile (20 ml) was heated at reflux for 12 hours. After filtration, the solvent was removed under vacuum and the crude residue was dissolved in $CH_2Cl_2$ (20 ml, washed with brine (15 ml), dried over $Na_2SO_4$ and evaporated at reduced pressure to give 1.17 g (90.2%) of the title compound.

C) 1-[3-[(4-Hydroxybutyl)amino]propyl]morpholine. To an ice cold solution of $LiAlH_4$ (0.48 g, 12.7 mmol) in anhydrous THF (20 ml) under nitrogen 1-{3-[(4-hydroxybutyl)amnino]-propionyl}morpholine (1.17 g, 5.08 mmol) in THF (10 ml) was added dropwise. The reaction was allowed to rise to room temperature and stirred for 3 hours under nitrogen, quenched by the sequential addition of water (0.5 ml), 15% aqueous sodium hydroxide NaOH (0.5 ml) and water (1.5 ml) again. The mixture was filtered through a Celite pad and then washed with $Et_2O$ (3×10 ml). The filtrate dried over anhydrous sodium sulphate and evaporated in vacuum yielded 0.63 g (57.3%) of the title compound.

Preparation 10

A) 3-[4-(2-Pyrimidinyl)piperazine-1-yl]propanamide. A mixture of 2.13 g (100 mmol) of 1-(2-pyrimidinyl) piperazine dihydrochloride, 1.07 g (100 mmol) 3-chloropropionamide, 3 ml triethylamine and 50 ml isopropyl alcohol was heated under stirring in a closed vessel at 120° C. during one night. After cooling, the solvent was concentrated in vacuo, the residue dissolved in 100 ml water and made alkaline with NaOH. The mixture was thoroughly extracted with ethyl acetate, dried over $MgSO_4$ and concentrated in vacuo. The residue was triturated with diethyl ether to afford 2 g (85%) of the title compound as crystals.

$^1$H NMR (CDCl$_3$) δ2.45 (t, 2H); 2.57 (t, 4H); 2.69 (t, 2H); 3.85 (t, 4H); 5.51 (s, broad band, 1H); 6.51 (t, broad band, 1H); 7.96 (s, broad band, 1H); 8.31 (d, 2H).

B) 3-[4-(2-Pyrimidinyl)piperazine-1-yl] propanamine. Two grams (85 mmol) of 3-[4-(2-pyrimidinyl)piperazine-1-yl]propanamide were suspended in 20 ml THF and 58 mg (170 mmol) lithium aluminium hydride were added. The mixture was stirred at room temperature for 0.5 hours and at reflux for 4 additional hours. The reaction was quenched with 58 microliters of water and 58 microliters of 15% aqueous NaOH. The mixture was filtered over Clarcel (filtration aid) and concentrated in vacuo. The crude residue was used in the next step without further purification.

EXAMPLE 1

Methyl (2Z,4E)-5-(2-indolyl)-2-methoxy-2,4-pentadienoate. Method A. A solution of 3-(2-indolyl)-2-propenaldehyde (2.5 g, 14.6 mmol) in anhydrous THF (150 ml) under nitrogen was treated with methyl 2-methoxy-2-(triphenylphosphonium)acetate bromide (*Chem. Ber.*, 97, 1713 (1964)) (6.5 g, 14.6 mmol) and DBU (2.18 ml, 14.6 mmol). The reaction mixture was stirred at 50° C. for 2 h, allowed to cool, diluted with $Et_2O$ (100 ml) and filtered. The filtrate was washed with 10% aqueous HCl (50 ml), saturated solution of $NaHCO_3$ (50 ml) and brine (50 ml), dried over $Na_2SO_4$ and evaporated under vacuum. The residue was purified by flash-chromatography (hexane/EtOAc 7:3) to afford a solid residue which, after trituration with isopropyl ether, yielded 2.57 g (68.5%) of the title compound, m.p.=117–119° C.

$^1$H-NMR (acetone-d$_6$): 10.60 (br s, 1H); 7.52 (d, 1H); 7.36 (dd, 1H); 7.19 (dd, 1H); 7.14 (ddd, 1H); 7.00 (ddd, 1H); 6.99 (d, 1H); 6.89 (d, 1H); 6.65 (d, 1H); 3.75 (s, 3H); 3.74 (s, 3H).

MS (TSP): 258 (MH)$^+$

Method B. An oil dispersion of 60% NaH (2.7 g, 67.5 mmol) was washed with pentane (2×5 ml) and then suspended in anhydrous THF (150 ml) under nitrogen. Trimethyl 2-methoxyphosphonoacetate (4.5 g, 21.2 mmol), dissolved in dry THF (50 ml) was added dropwise and the reaction mixture was stirred at 40° C. for 45 min. A solution of 3-(2-indolyl)-2-propenaldehyde (2.96 g, 17 mmol) in dry THF (40 ml) was added dropwise and the reaction mixture was stirred at 40° C. for 25 h. The reaction was quenched with water and extracted with $Et_2O$ (3×100 ml). The combined organic layers were washed with 10% aqueous HCl (50 ml), saturated solution of $NaHCO_3$ (50 ml) and brine (50 ml), dried over $Na_2SO_4$ and evaporated in vacuum. The residue was purified by flash-chromatography (hexane/ EtOAc 85:15) and triturated with isopropyl ether to afford 43 mg (1%) of the same compound obtained with the method A and 7 mg (0.15%) of methyl (2Z,4E)-2-methoxy-5-(1-methyl-2-indolyl)-2,4-pentadienoate, m.p.=93–94° C.

Methyl (2Z,4E)-2-methoxy-5-(1-methyl-2-indolyl)-2,4-pentadienoate: $^1$H-NMR (acetone-d$_6$): 7.53 (dt, 1H); 7.39 (dq, 1H); 7.27 (dd, 1H); 7.18 (d, 1H); 7.17 (ddd, 1H); 7.03 (ddd, 1H);6.94 (d, 1H); 6.94 (s, 1H); 3.85 (s, 3H); 3.79 (s, 6H).

MS (EI, 70 eV, 200 mA): 271(M$^+$); 239; 212.

EXAMPLE 2

Methyl (2Z,4E)-2-methoxy-5-(5-methoxy-2-indolyl)-2,4-pentadienoate. A solution of (E)-3-(5-methoxy-2-indolyl)-2-propenaldehyde (0.45 g, 2.24 mmol) in 10 ml of anhydrous THF was dropped into a suspension of trimethyl 2-methoxyphosphonoacetate (0.7 g, 3.3 mmol) and 60% oil dispersion of NaH (0.22 g, 5.5 mmol) in 10 ml of anhydrous THF according to the procedure of Example 1B. After work-up and purification by column chromatography, 29 mg (4.5 %) of the title compound, m.p.=150–151° C. and 25 mg (3.7%) of methyl (2Z,4E)-2-methoxy-5-(5-methoxy-1-methyl-2-indolyl)-2,4-pentadienoate, m.p.=160–162° C., were obtained.

Methyl (2Z,4E)-2-methoxy-5-(5-methoxy-2-indolyl)-2,4-pentadienoate: $^1$H-NMR (acetone-d$_6$): 10.45 (br s, 1H); 7.25

(d, 1H); 7.14 (dd, 1H); 7.03 (d, 1H); 6.95 (d, 1H); 6.87 (d, 1H); 6.79 (dd, 1H); 6.59 (d, 1H); 3.79 (s, 3H); 3.77 (s, 3H); 3.74 (s, 3H).

MS (EI, 70 eV, 200 mA): 287 (M$^+$); 255; 228.

Methyl (2Z,4E)-2-methoxy-5-(5-methoxy-1-methyl-2-indolyl)-2,4-pentadienoate: $^1$H-NMR (acetone-d$_6$): 7.29 (d, 1H); 7.22 (dd, 1H); 7.14 (d, 1H); 7.02 (d, 1H); 6.93 (d, 1H); 6.86 (s, 1H); 6.83 (dd, 1H); 3.81 (s, 3H); 3.79 (s, 3H); 3.78 (s, 3H); 3.77 (s, 3H). MS (EI, 70 eV, 200 mA): 301 (M$^+$); 269; 242.

EXAMPLE 3

Methyl (2Z,4E)-4-ethyl-5-(2-indolyl)-2-methoxy-2,4-pentadienoate. (E)-2-Ethyl-3-(2-indolyl)-2-propenaldehyde (0.3 g, 1.5 mmol) and DBU (0.45 ml, 3 mmol) were treated with methyl 2-methoxy-2-(triphenylphosphonium)acetate bromide (0.67 g, 1.5 mmol) according to the procedure of Example 1A to afford 40 mg (9.3%) of the title compound, m.p.=93–95° C.

$^1$H-NMR (CDCl$_3$): 8.08 (br s, 1H); 7.61 (d, 1H); 7.36 (d, 1H); 7.20 (ddd, 1H); 7.11 (ddd, 1H); 6.81 (s, 1H); 6.71 (d, 1H); 6.67 (s, 1H); 3.85 (s, 3H); 3.79 (s, 3H); 2.80 (q, 2H); 1.29 (t, 3H). MS (EI, 70 eV, 200 mA): 285 (M$^+$); 253; 226.

EXAMPLE 4

Methyl (2Z,4E)-5-(5-chloro-2-indolyl)-2-methoxy-2,4-pentadienoate. 5-Chloroindole-2-carboxaldehyde was prepared starting from ethyl 5-chloroindole-2-carboxylate (7.4 g, 33 mmol) according to the procedure of Preparation 1, obtaining 2 g of a yellow solid, m.p.=208–209° C. The aldehyde (1.2 g, 6.7 mmol) was transformed in (E)-3-(5-chloro-2-indolyl)-2-propenaldehyde through the reaction with (formylmethylene)triphenylphosphorane (2 g, 6.7 mmol) following the procedure described in Preparation 2, obtaining 0.5 g of yellow powder, m.p.=207–209° C. (E)-3-(5-Chloro-2-indolyl)-2-propenaldehyde (0.5 g, 2.4 mmol) and DBU (0.75 ml, 5 mmol) were treated with methyl 2-methoxy-2-(triphenylphosphonium)acetate bromide (2.16 g, 5 mmol) according to the procedure of Example 1A to afford 250 mg (47%) of the title compound, m.p.=166–168° C.

$^1$H-NMR (acetone-d$_6$): 10.76 (br s, 1H); 7.54 (d, 1H); 7.36 (d, 1H); 7.21 (dd, 1H); 7.11 (dd, 1H); 6.98 (d, 1H); 6.87 (d, 1H); 6.65 (s, 1H); 3.79 (s, 3H); 3.72 (s, 3H).

MS (EI, 70 eV, 200 mA): 291 (M+), 259, 197, 59.

EXAMPLE 5

Methyl (2Z,4E)-5-(4,5-dichloro-2-indolyl)-2-methoxy-2,4-pentadienoate and Methyl (2Z,4E)-5-(5,6-dichloro-2-indolyl)-2-methoxy-2,4-pentadienoate.

A) 3,4-Dichlorophenylhydrazine (25 g, 117 mmol) was treated with ethyl pyruvate (12.8 ml, 117 mmol) in ethanol (300 ml) giving, after filtration, 30 g of yellow powder, m.p.=108–113° C. This compound (10 g, 36.3 mmol) was cyclised refluxing for 3 h in toluene (300 ml) in presence of anhydrous p-toluensulfonic acid (10 g, 58 mmol) obtaining 4.4 g (47%) of the mixture of ethyl 4,5-dichloroindol-2-carboxylate and ethyl 5,6-dichloroindol-2-carboxylate.

B) The mixture prepared before (4.3 g, 16.7 mmol) was transformed into the mixture of 4,5-dichloroindol-2-carboxaldehyde and 5,6-dichloroindol-2-carboxaldehyde according to the procedure of Preparation 1, obtaining 2.1 g of a yellow powder. This compound (2.1 g, 10 mmol) was treated with (formylmethylene)triphenylphosphorane (3 g, 10 mmol) following the procedure described in Preparation 3, obtaining 0.9 g of a yellow solid as a mixture of (E)-3-(4,5-dichloro-2-indolyl)-2-propenaldehyde and (E)-3-(4,5-dichloro-2-indolyl)-2-propenaldehyde. This mixture (0.8 g, 3.3 mmol) and DIPEA (1.13 ml, 6.6 mmol) were treated with methyl 2-methoxy-2-(triphenylphosphonium) acetate bromide (2.97 g, 6.6 mmol) according to the procedure of Example 1A to afford after column chromatography separation 20 mg of pure 4,5-dichloro isomer, m.p.= 202–204° C. and 11 mg of pure 5,6-dichloro isomer, m.p.= 206–208° C.

Methyl (2Z,4E)-5-(4,5-dichloro-2-indolyl)-2-methoxy-2,4-pentadienoate: $^1$H-NMR (CDCl$_3$) 8.38 (br s, 1H); 7.23 (d, 1H); 7.17 (d, 1H); 7.01 (dd, 1H); 6.86 (d, 1H); 6.78 (d, 1H); 6.72 (d, 1H); 3.84 (s, 3H); 3.83 (s, 3H).

MS (EI, 70 eV, 200 mA): 325 (M$^+$).

Methyl (2Z,4E)-5-(5,6-dichloro-2-indolyl)-2-methoxy-2,4-pentadienoate: $^1$H-NMR (acetone-d$_6$) 10.86 (br s, 1H); 7.73 (dd, 1H); 7.67 (s, 1H); 7.51 (s, 1H); 6.76 (d, 1H); 6.52 (s, 1H); 6.24 (d, 1H); 3.82 (s, 3H); 3.70 (s, 3H).

MS (EI, 70 eV, 200 mA): 325 (M$^+$).

EXAMPLE 6

Methyl (2Z,4E)-5-(5,6-dichloro-2-indolyl)-2-methoxy-2,4-pentadienoate. To a solution of 11.5 g of the (E) 3-(5,6-dichloro-2-indolyl)-2-propenaldehyde (47.89 mmol), prepared as described in Preparation 8, in 200 ml of THF, 23.5 g of methyl 2-methoxy-2-(triphenyl-phosphonium)acetate bromide (52.7 mmol) and 7.84 ml of DBU (52.7 mmol) were added. The reaction was refluxed for 1.5 h. The solvent was removed under reduced pressure and the crude compound was purified by flash chromatography (Hexane/AcOEt 7:3). After trituration with isopropyl ether, 14 g (89.6%) of the title compound was obtained, m.p.=205–206° C., identical to that obtained in Example 5.

EXAMPLE 7

Methyl (2Z,4E)-5-[2-(3-methylindolyl)]-2-methoxy-5-phenyl-2,4-pentadienoate. A solution of 90 mg of (2E)-3-(3-methylindolyl)-3-phenyl-2-propenaldehyde (0.344 mmol) in dichloromethane was treated under nitrogen with methyl 2-methoxy-2-(triphenylphosphonium)acetate bromide (0.306 g, 0.69 mmol) and DBU (0.103 ml, 0.69 mmol) as described in Example 1A. After the work-up of the reaction the residue was chromatographed over silica gel (EtOAc/hexane 2:8) obtaining 30 mg (25.1%) of the title compound as a yellow solid, mp.=130–133° C.

$^1$H-NMR (acetone-d$_6$): 10.05 (br s, 1H); 7.53–7.45(m, 4H); 7.36–7.29 (m, 3H); 7.13 (d, 1H); 7.13 (ddd, 1H); 7.01 (ddd, IH); 6.80 (d, 1H); 3.75 (s, 3H); 3.67 (s, 3H); 1.89 (s, 3H).

MS (EI, 70 eV, 200 mA): 347 (M+); 315; 288; 273.

EXAMPLE 8

Methyl (2Z,4E)-5-(1-acetyl-3-indolyl)-2-methoxy-2,4-pentadienoate. To an ice-cold stirred solution of trimethyl (Z)-2-methoxyphosphono-2-butenoate (2 g, 8.4 mmol) in dry THF (38 ml) and under nitrogen, DBU (1.25 ml, 8.4 mmol) was added dropwise. After 15 minutes the reaction was allowed to reach room temperature and after 30 minutes a suspension of N-acetylindole-3-carboxaldehyde (1.2 g, 6.41 mmol) in dry THF (13 ml) was added at 0° C. The reaction was refluxed for 3 h and then quenched with 10% aqueous citric acid and extracted with ethyl acetate. The organic layer was washed with brine, dried over Na$_2$SO$_4$ and evaporated under reduced pressure. The crude product was purified by flash-chromatography (light petroleum/EtOAc 4:1) yielding 30 mg of the title compound (1.5%), m.p.= 107–108° C.

$^1$H-NMR (CDCl$_3$): 8.47 (d, 1H); 7.82 (dd, 1H); 7.60 (s, 1H); 7.41 (ddd, 1H); 7.38 (ddd, 1H); 7.26 (dd, 1H); 6.92 (d, 1H); 6.91 (d, 1H); 3.84 (s, 3H); 3.83 (s, 3H); 2.68 (s, 3H).

MS (EI, 70 eV, 200 mA): 299 (M$^+$); 257; 225.

EXAMPLE 9

(2Z,4E)-N-Butyl-5-(2-indolyl)-2-methoxy-2,4-pentadienamide. A 2M solution of trimethylaluminium in toluene (0.4 ml) was added at room temperature under nitrogen to a solution of butylamine (0.04 ml, 0.39 mmol) in dichloromethane (10 ml). Stirring was continued for 30 minutes and methyl (2Z,4E)-5-(2-indolyl)-2-methoxy-2,4-pentadienoate (0.1 g, 0.39 mmol) was added. The solution was refluxed for 5 hours; after cooling to 10° C., the reaction was quenched with 10% HCl and the separated organic layer was washed with a saturated solution of $NaHCO_3$ and water, dried over $Na_2SO_4$ and evaporated under vacuum. The solid residue was triturated with isopropyl ether, to give 55 mg (47.3%) of the title compound as a solid, m.p.=185–186° C.

$^1$H-NMR (acetone-$d_6$): 10.54 (br s, 1H); 7.51 (d, 1H); 7.41 (br s, 1H); 7.34 (d, 1H); 7.16 (dd, 1H); 7.10 (ddd, 1H); 7.00 (ddd, 1H); 6.89 (d, 1H); 6.79 (d, 1H); 6.61 (s, 1H); 3.79 (s, 3H); 3.30 (dt, 2H); 1.59–1.49 (m, 2H);1.42–1.30 (m, 2H); 0.91 (t, 3H).

MS (EI, 70 eV, 200 mA): 298(M+); 266; 198; 57.

EXAMPLE 10

(2Z,4E)-N-Benzyl-5-(2-indolyl)-2-methoxy-2,4-pentadienamide. This compound was prepared following the same procedure of Example 9 and starting from (2Z,4E)-5-(2-indolyl)-2-methoxy-2,4 pentadienoate (0.1 g, 0.39 mmol), benzylamine (0.043 ml, 0.39 mmol) and a solution of 2M trimethylaluminium in toluene (0.4 ml, 0.8 mmol). After crystallisation from isopropanol, 42 mg (32.4%) of the title compound were obtained, m.p.=204–205° C. $^1$H-NMR (acetone-$d_6$): 10.55 (br s, 1H); 7.94 (br t, 1H); 7.51 (d, 1H); 7.38–7.21 (m, 6H); 7.18 (dd, 1H); 7.11 (ddd, 1H); 6.99 (ddd, 1H); 6.91 (d, 1H); 6.85 (d, 1H); 6.61 (s, 1H); 4.50 (d, 2H); 3.79 (s, 3H).

MS (EI, 70 eV, 200 mA): 332 (M$^+$); 300; 198; 91.

EXAMPLE 11

(2Z,4E)-5-(2-Indolyl)-2-methoxy-2,4-pentadienoic acid. To a solution of KOH (0.26 g, 4.7 mmol) in methanol (13 ml), methyl (2Z,4E)-5-(2-indolyl)-2-methoxy-2,4-pentadienoate (0.3 g, 1.17 mmol) was added and the solution was heated at 50° C. for 1 hour under nitrogen. The solvent was removed under vacuum and the residue was dissolved in water (20 ml) and washed with isopropyl ether. The aqueous phase was adjusted to pH 5 with 10% HCl and then extracted with ethyl acetate. The organic layer was washed with water, dried over $Na_2SO_4$ and the solvent removed under reduced pressure obtaining, after trituration with isopropyl ether, 0.15 g (52.7%) of the title compound as a solid, m.p.=189–190° C.

$^1$H-NMR (acetone-$d_6$): 10.60 (br s, 1H); 7.53 (d, 1H); 7.36 (dd, 1H); 7.20 (dd, 1H); 7.03 (ddd, 1H); 7.00 (ddd, 1H); 6.99 (d, 1H); 6.92 (d, 1H); 6.65 (d, 1H); 3.75 (s, 3H).

MS (EI, 70 eV, 200 mA): 243 (M$^+$); 211; 198.

EXAMPLE 12

(2Z,4E)-N,N-Diethyl-5-(2-indolyl)-2-methoxy-2,4-pentadienamide. To a solution of (2Z,4E)-5-(2-indolyl)-2-methoxy-2,4-pentadienoic acid (0.1 g, 0.41 mmol), diethylamine (0.042 ml, 0.41 mmol) and 1-hydroxybenzotriazole (55 mg, 0.41 nmol) in DMF/THF 1:1 (50 Ml), DCC (0.093 g, 0.45 mmol) was added at 0° C. The resulting solution was stirred at room temperature for 48 hours. The solvent was removed under reduced pressure and the residue was dissolved in dichloromethane, washed successively with 10% HCl, saturated solution of $NaHCO_3$ and water, dried and evaporated under vacuum. The crude material was purified by column chromatography (EtOAc/hexane 4:6) and triturated with isopropyl ether to yield 21 mg (17.2%) of the title compound as a light yellow solid, m.p.=141–143° C.

$^1$H-NMR (acetone-$d_6$): 10.45 (br s, 1H); 7.49 (d, 1H); 7.32 (dd, 1H); 7.11 (dd, 1H); 7.08 (ddd, 1H); 6.98 (ddd, 1H); 6.66 (d, H); 6.49 (d, 1H); 5.74 (dd, 1H); 3.65 (s, 3H); 3.45 (q, 4H); 1.20 (t, 6H).

MS (EI, 70 eV, 200 mA): 298 (M$^+$); 266.

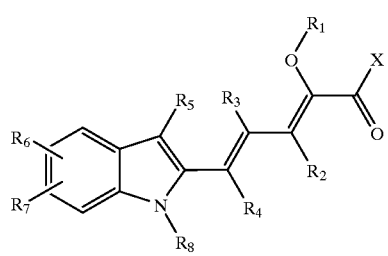

| Ex. No. | Name | X | R1 | R2 | R3 |
|---|---|---|---|---|---|
| 13 | (2Z,4E)-5-(5-Chloro-2-indolyl))-2-methoxy-N-phenylmethyl-2,4-pentadienamide | HN-CH$_2$-C$_6$H$_5$ | Me | —H | —H |
| 14 | (2Z,4E)-5-(5-Chloro-2-indolyl)-2-methoxy-N-(3,4-dimethoxy-phenylethyl)-2,4-pentadienamide | HN-CH$_2$CH$_2$-C$_6$H$_3$(OMe)$_2$ | Me | —H | —H |

-continued

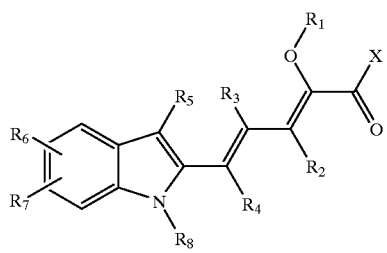

| | | | X | $R_1$ | $R_2$ | $R_3$ |
|---|---|---|---|---|---|---|
| 15 | (2Z,4E)-5-(5-Chloro-2-indolyl)-2-methoxy-N-(3-pyridylmethyl)-2,4-pentadienamide | 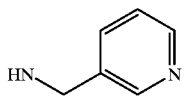 | | Me | —H | —H |
| 16 | (2Z,4E)-5-(5-Chloro-2-indolyl)-2-methoxy-N-(3,4-dimethoxyphenyl-methyl)-2,4-pentadienamide | 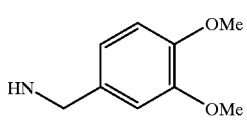 | | Me | —H | —H |
| 17 | (2Z,4E)-5-(5-Chloro-2-indolyl)-2-methoxy-N-(3,5-dimethoxyphenyl-methyl-2,4-pentadienamide | 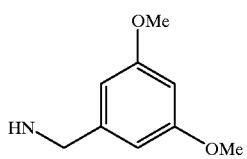 | | Me | —H | —H |
| 18 | Methyl(2Z,4E)-5-(5-fluoro-2-indolyl)-2-methoxy-2,4-pentadienoate | —OMe | | Me | —H | —H |
| 19 | Methyl(2Z,4E)-5-(5-nitro-2-indolyl)-2-methoxy-2,4-pentadienoate | —OMe | | Me | —H | —H |
| 20 | (2Z,4E)-5-(5-Chloro-2-indolyl)-N-2,3-dihydroxypropyl-2-methoxy-N-phenylmethyl-2,4-pentadienamide | 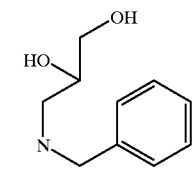 | | Me | —H | —H |
| 21 | (2Z,4E)-5-(5-Chloro-2-indolyl)-2-methoxy-N-phenyl-2,4-pentadienamide | 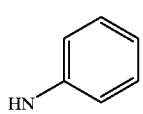 | | Me | —H | —H |
| 22 | Methyl (2Z,4E)-2-methoxy-5-[(1-methylpropyl)-2-indolyl]-2,4-pentadienoate | —OMe | | Me | —H | —H |
| 23 | (2Z,4E)-5-(5-Chloro-2-indolyl)-2-methoxy-2,4-pentadienoic acid | —OH | | Me | —H | —H |
| 24 | (2Z,4E)-5-(5-Chloro-2-indolyl)-N-(4-hydroxybutyl)-2-methoxy-2,4-pentadienamide | 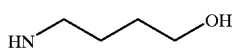 | | Me | —H | —H |
| 25 | (2Z,4E)-5-(5-Chloro-2-indolyl)-N,N-diethyl-2-methoxy-2,4-pentadienamide |  | | Me | —H | —H |

-continued

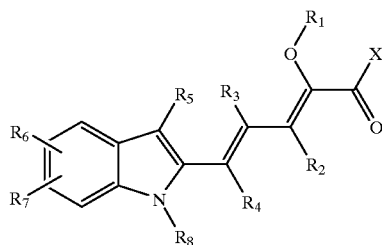

| # | Name | X | | | |
|---|---|---|---|---|---|
| 26 | (2Z,4E)-5-(5-Chloro-2-indolyl)-N-[3-(diethylamino)-propyl]-2-methoxy-2,4-pentadienamide | HN~~~N(Et)₂ | Me | —H | —H |
| 27 | (2Z,4E)-5-(5-Chloro-2-indolyl)-N-ethyl-1-methoxy-2,4-pentadienamide | HN~Et | Me | —H | —H |
| 28 | (2Z,4E)-5-(5-Chloro-2-indolyl)-2-methoxy-2,4-pentadienamide | —NH₂ | Me | —H | —H |
| 29 | (2Z,4E)-5-(5-Chloro-2-indolyl)-2-methoxy-N,N-dimethoxyethyl-2,4-pentadienamide | N(CH₂CH₂OMe)₂ | Me | —H | —H |
| 30 | Ethyl(2Z,4E)-5-(5-chloro-2-indolyl)-2-ethoxy-2,4-pentadienoate | —OEt | Et | —H | —H |
| 31 | Methyl (2Z,4E)-5-(5,7-dichloro-2-indolyl)-2-methoxy-2,4-pentadienoate | —OMe | Me | —H | —H |
| 32 | Methyl(2Z,4E)-5-(6,7-dichloro-2-indolyl)-2-methoxy-2,4-pentadienoate | —OMe | Me | —H | —H |
| 33 | (2Z,4E)-5-(5-Chloro-2-indolyl))-2-methoxy-N-(3-pyridyl)-2,4-pentadienamide | HN-(3-pyridyl) | Me | —H | —H |
| 34 | (2Z,4E)-5-(5,6-Dichloro-2-indolyl)-N-[3-(diethylamino)-propyl]-2-methoxy-2,4-pentadienamide | HN~~~N(Et)₂ | Me | —H | —H |
| 35 | Methyl(2Z,4E)-2-methoxy-5-[(5,6-dimethoxy-3-(4-methoxyphenyl)-2-indolyl]-2,4-pentadienoate | —OMe | Me | —H | —H |
| 36 | Methyl(2Z,4E)-5-(5-chloro-7-methyl-2-indolyl)-2-methoxy-2,4-pentadienoate | —OMe | Me | —H | —H |
| 37 | (2Z,4E)N-(4-Aminophenylmethyl-5-(5-chloro-2-indolyl)-2-methoxy-2,4-pentadienamide | —HNCH₂-C₆H₄-NH₂ | Me | —H | —H |
| 38 | Diethyl(2Z,4E)-2-[[4-[5-(5-chloro-2-indolyl)-2-methoxy-2,4-pentadienoyl]-amino]2-butenyl]-2-hydroxy-propanedioate | HN-CH₂-CH=CH-CH₂-C(OH)(COOEt)₂ | Me | —H | —H |

-continued

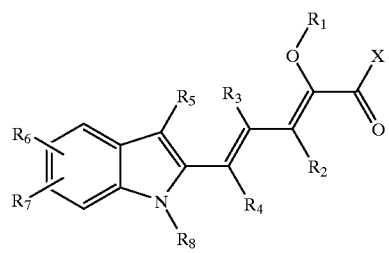

| | | X | $R_1$ | $R_2$ | $R_3$ |
|---|---|---|---|---|---|
| 39 | Tetraethyl(2Z,4E)-4-[5-(5-chloro-2-indolyl)-2-methoxy-2,4-pentadienylcarbonylamino]-1,1-butanediphosponate | 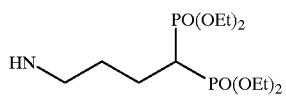 | Me | —H | —H |
| 40 | Tetramethyl(2Z,4E)-5-[5-(5-chloro-2-indolyl)-2-methoxy-2,4-pentadienoyl]amino]-1-hydroxy-1,1-pentanediphosphonate | 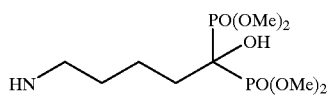 | Me | —H | —H |
| 41 | Methyl(2Z,4E)-2methoxy-5-(5,6-dimethoxy-2-indolyl)-2,4-pentadienoate | —OMe  | Me | —H | —H |
| 42 | (2Z,4E)-5-(5,6-Dichloro-2-indolyl)-2-methoxy-2,4-pentadienoic acid | —OH  | Me | —H | —H |
| 43 | Methyl(2Z,4E)[[3-[5-(5,6-dichloro-2-indolyl)2-methoxy-2,4-pentadienoylamino]propyl]methoxycarbonylmethyl-amino]acetate | 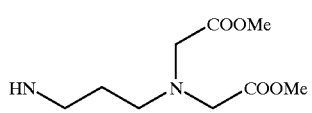 | Me | —H | —H |
| 44 | (2Z,4E)-5-(5,6-Dichloro-2-indolyl)-2-methoxy-N-(3-pyridyl)-2,4-pentadienamide | 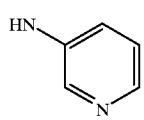 | Me | —H | —H |
| 45 | (2Z,4E)[[3-[5-(5,6-Dichloro-2-indolyl)2-methoxy-2,4-pentadienoyl-amino]propyl]methoxycarbonylmethyl-amino]acetic acid hydrochloride | 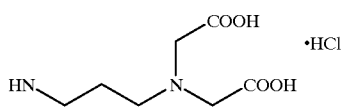 | Me | —H | —H |
| 46 | (2Z,4E)-5-(5,6-Dichloro-2-indolyl)-N-[2-(diethylamino)-ethyl]-2-methoxy-2,4-pentadienamide | 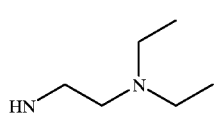 | Me | —H | —H |
| 47 | Ethyl(2Z,4E)-4-[[5-(5,6-dichloro-2-indolyl)-2-methoxy-2,4-pentadienoyl]amino]-1-piperidineacetate | 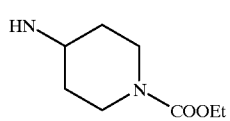 | Me | —H | —H |
| 48 | (2Z,4E)-5-(5,6-Dichloro-2-indolyl)-2-methoxy-N-(2-pyridyl)-2,4-pentadienamide | 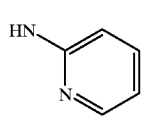 | Me | —H | —H |

-continued

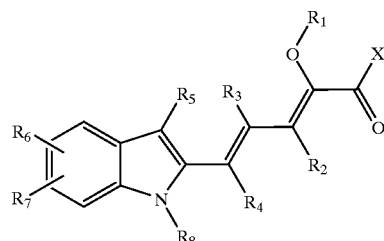

| | | | | | | |
|---|---|---|---|---|---|---|
| 49 | (2Z,4E)-5-(5,6-Dichloro-2-indolyl)-N-[3-(1H-imidazol-1-yl)-propyl]-2-methoxy-2,4-pentadienamide | 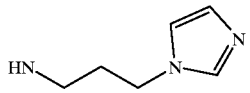 | | Me | —H | —H |
| 50 | (2Z,4E)-N-[(S)-1-Azabicyclo[2.2.2]octan-3-yl]-5-(5,6-dichloro-2-indolyl)-2-methoxy-2,4-pentadienamide | 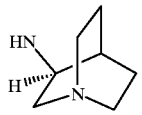 | | Me | —H | —H |
| 51 | (2Z,4E)-5-(5,6-Dichloro-2-indolyl)-N-[3-(morpholino)propyl]-2-methoxy-2,4-pentadienamide | 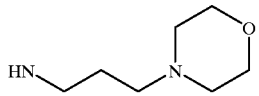 | | Me | —H | —H |
| 52 | (2Z,4E)-5-(5,6-Dichloro-2-indolyl)-N-[2-(5-diethylamino)pentyl]-2-methoxy-2,4-pentadienamide | 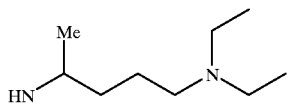 | | Me | —H | —H |
| 53 | (2Z,4E)-5-(5,6-Dichloro-2-indolyl)-N-[2-(1-piperidinyl)-ethyl]-2-methoxy-2,4-pentadienamide | 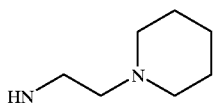 | | Me | —H | —H |
| 54 | (2Z,4E)-5-(5,6-Dichloro-2-indolyl)-2-methoxy-N-[2-[2-(1-methyl)pyrrolidinyl]ethyl]-2,4-pentadienamide | 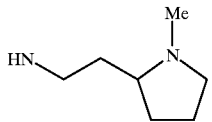 | | Me | —H | —H |
| 55 | (2Z,4E)-5-(5,6-Dichloro-2-indolyl)-N-[4,5-dihydro-2-thiazolyl)-2-methoxy-2,4-pentadienamide | 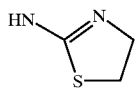 | | Me | —H | —H |
| 56 | (2Z,4E)-5-(5,6-Dichloro-2-indolyl)-2-methoxy-N-[4-(2,2,6,6-tetramethyl)piperidinyl]-2,4-pentadienamide | 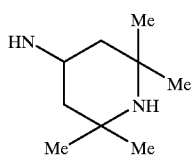 | | Me | —H | —H |

-continued

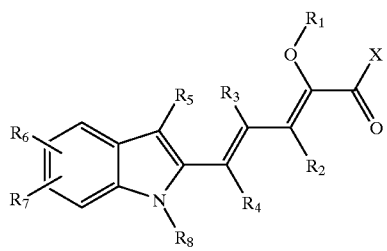

| | | | | | |
|---|---|---|---|---|---|
| 57 | (2Z,E)-5-(5,6-Dichloro-2-indolyl)-2-methoxy-N-[5-(2-methoxy)pyridyl]-2,4-pentadienamide | 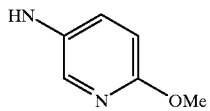 | Me | —H | —H |
| 58 | 3-(Diethylamino)propyl(2Z,4E)-5-(5,6-dichloro-2-indolyl)-2-methoxy-2,4-pentaidenoate | 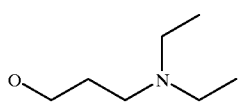 | Me | —H | —H |
| 59 | (2Z,4E)-5-(5,6-Dichloro-2-indolyl)-2-methoxy-N[3-[1-(2-methyl)piperidin-yl]-propyl]-2,4-pentadienamide | 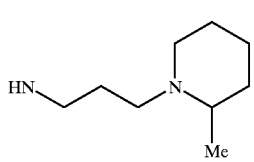 | Me | —H | —H |
| 60 | (2Z,4E)-5-(5,6-Dichloro-2-indolyl)-2-methoxy-N-[1-(4-methylpiperazinyl)]-2,4-pentadienamide | 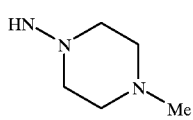 | Me | —H | —H |
| 61 | Methyl(2Z,4E)-5-[2-(6-chloroindolyl)-2-methoxy-2,4-pentadienoate | —OMe | Me | —H | —H |
| 62 | (2Z,4E)-5-(5,6-Dichloro-2-indolyl)-2-methoxy-N-[3-[N-ethyl-N-(phenylmethylamino]-propyl]-2,4-pentadienamide | 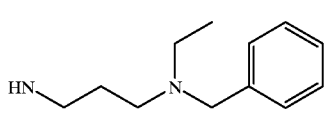 | Me | —H | —H |
| 63 | (2Z,4E)-N-[1-Azabicyclo[2.2.2]octan-3-yl]-5-(5,6-dichloro-2-indolyl)-2-methoxy-2,4-pentadienamide | 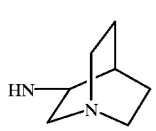 | Me | —H | —H |
| 64 | (2Z,4E)-5-(5,6-Dichloro-2-indolyl)-2-methoxy-N-methyl-N-(dimethylamino-2,2-dimethylpropyl)-2,4-pentadienamide |  | Me | —H | —H |
| 65 | (2Z,4E)-5-(5,6-Dichloro-2-indolyl)-2-methoxy-N-(2-pyrimidinyl)-2,4-pentadienamide | 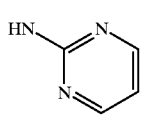 | Me | —H | —H |

-continued

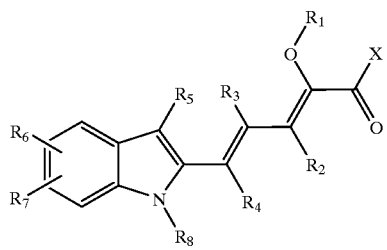

| | | | X | $R_1$ | $R_2$ | $R_3$ |
|---|---|---|---|---|---|---|
| 66 | (2Z,4E)-6-(5,6-dichloro-2-indolyl)-N-[8-methyl-8-azabicyclo[3.2.1]oct-3β-yl]-2-methoxy-2,4-pentadienamide | 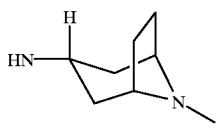 | | Me | —H | —H |
| 67 | (2Z,4E)-5-(5,6-Dichloro-2-indolyl)-2-methoxy-N-[3-[1-(4-methyl)piperazinyl]-propyl]-2,4-pentadienamide | 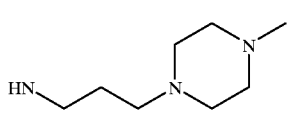 | | Me | —H | —H |
| 68 | (2Z,4E)-5-(5,6-Dichloro-2-indolyl)-N-[1-[5-(5,6-dichloro-2-indolyl)-2-methoxy-1-oxo-2,4-pentadieny-1-yl]piperidin-4-yl]methyl]-2-methoxy-2,4-pentadienamide | 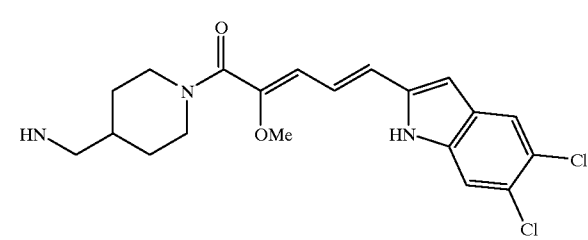 | | Me | —H | —H |
| 69 | (2Z,4E)-5-(5,6-Dichloro-2-indolyl)-2-methoxy-N-[3-[2-(1,2,3,4-tetrahydroisoquinolinyl)]propyl]-2,4-pentadienamide | 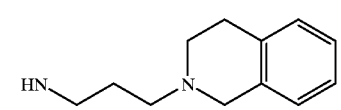 | | Me | —H | —H |
| 70 | (2Z,4E)-5-(5,6-Dichloro-2-indolyl)-2-methoxy-N-[4-(1-methyl)-piperidinyl]-2,4-pentadienamide | 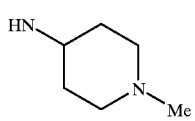 | | Me | —H | —H |
| 71 | (2Z,4E)-5-(5,6-Dichloro-2-indolyl)-2-methoxy-N-(1H-pyrazolo[3,4-d]pyrimidin-4-yl)-2,4-pentadienamide | 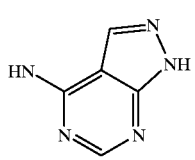 | | Me | —H | —H |
| 72 | (2Z,4E)-5-(5,6-Dichloro-2-indolyl)-2-methoxy-N-(5-quinolinyl)-2,4-pentadienamide | 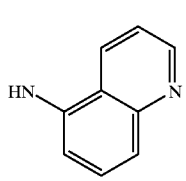 | | Me | —H | —H |

-continued

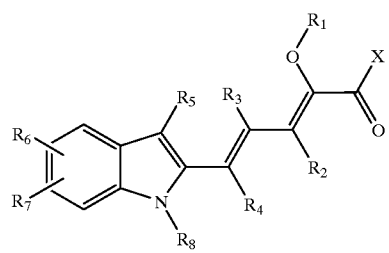

| | | | R1 | R2 | R3 |
|---|---|---|---|---|---|
| 73 | (2Z,4E)-5-(5,6-Dichloro-2-indolyl))-2-methoxy-N-[5-(2-chloro)pyridyl]-2,4-pentadienamide | 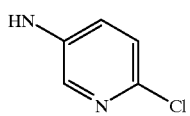 | Me | —H | —H |
| 74 | Diethyl(2Z,4E)-[4-[[[5-(5,6-dichloro-2-indolyl)-2-methoxy-2,4-pentadienoyl]amino]methyl]phenyl]hydroxypropanedioate | 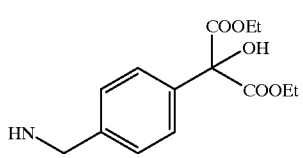 | Me | —H | —H |
| 75 | (2Z,4E)-5-(5,6-Dichloro-2-indolyl)-2-methoxy-N-[(4-dimethylamino)phenyl]-2,4-pentdienamide | 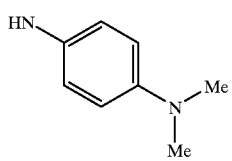 | Me | —H | —H |
| 76 | N-[(2Z,4E)-5-(5,6-Dichloro-2-indolyl)2-methoxy-2,4-pentadienoyl]-N'-[1-[2-(2-hydroxyethoxy)ethyl]]piperazine | 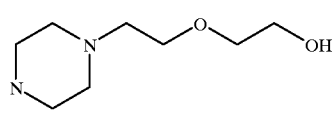 | Me | —H | —H |
| 77 | (2Z,4E)-5-(5,6-Dichloro-2-indolyl)--N-(4-hydroxybutyl)-2-methoxy-N-[3-(morpholino)propyl]-2,4-pentadienamide | 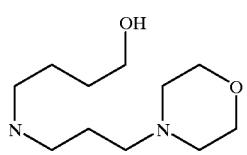 | Me | —H | —H |
| 78 | (2Z,4E)-5-(5,6-Dichloro-2-indolyl)-N-[3-(diethylamino)propyl]-N-methyl-2-methoxy-2,4-pentadienamide | 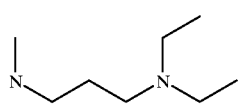 | Me | —H | —H |
| 79 | (2Z,4E)-5-(5,6-Dichloro-2-indolyl)-N-[(2,6-dimethyl)piperazin-4-yl]-2-methoxy-2,4-pentadienamide | 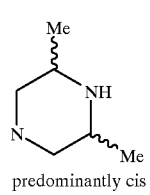
predominantly cis | Me | —H | —H |

-continued

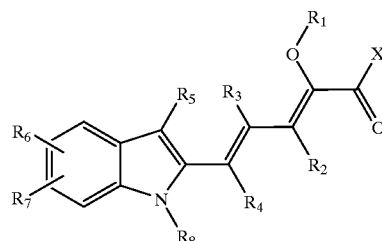

| | | | | R1 | R2 | R3 |
|---|---|---|---|---|---|---|
| 80 | (2Z,4E)-5-(5,6-Dichloro-2-indolyl)-2-methoxy-N-(7H-purin-2-yl)-2,4-pentadienamide | HN—[2-aminopurine] | | Me | —H | —H |
| 81 | (2Z,4E)-5-(5,6-Dichloro-2-indolyl)-2-methoxy-N-[2-(2-pyriyl)ethyl]-2,4-pentadienamide | HN—CH2CH2—(2-pyridyl) | | Me | —H | —H |
| 82 | (2Z,4E)-5-(5,6-Dichloro-2-indolyl)-2-methoxy-N-[(6-methoxy-3-pyridyl)methyl]-2,4-pentadienamide | HN—CH2—(6-methoxy-3-pyridyl) | | Me | —H | —H |
| 83 | (2Z,4E)-5-(5,6-Dichloro-2-indolyl)-2-methoxy-N-[3-(2,4,5-trimethyl-piperazin-1-yl)propyl]-2,4-pentadienamide | HN—(CH2)3—(2,4,5-trimethylpiperazin-1-yl) | | Me | —H | —H |
| 84 | (2Z,4E)-5-(5,6-Dichloro-2-indolyl)-2-methoxy-N-[3-[4-(2-pyrimidinyl)pipe-razin-1-yl]propyl]-2,4-pentadienamide | HN—(CH2)3—[4-(2-pyrimidinyl)piperazin-1-yl] | | Me | —H | —H |
| 85 | Methyl(2Z,4E)-5-[2-(5,6-dichloro-1-methylindolyl)]-2-methoxy-2,4-pentadienoate | OMe | | Me | —H | —H |
| 86 | Methyl(2Z,4E)-5-[2-(1-t-butoxycarbonylmethyl-5,6-dichloro)-1-indolyl]-2-methoxy-2,4-pentadienoate | OMe | | Me | —H | —H |
| 87 | (2Z,4E)-5-(5,6-Dichloro-2-indolyl)-2-methoxy-N-[(2,2,5,5-tetramethylpyrrolidin-3-yl)methyl]-2,4-pentadienamide | HN—CH2—(2,2,5,5-tetramethylpyrrolidin-3-yl) | | Me | —H | —H |

-continued

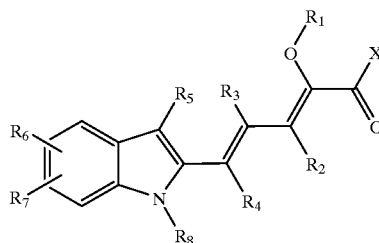

| | | | X | $R_1$ | $R_2$ | $R_3$ |
|---|---|---|---|---|---|---|
| 88 | (2Z,4E)-5-(5,6-Dichloro-2-indolyl)-2-methoxy-N-(6-methoxypyridazin-3-yl)-2,4-pentadienoate | 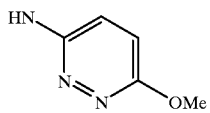 | | Me | —H | —H |
| 89 | Methyl(2Z,4E)-5-(3-ethyl-5,6-dichloro-2-indolyl)-2-methoxy-2,4-pentadienoate | OMe | | Me | —H | —H |
| 90 | (2Z,4E)-5-(5,6-Dichloro-2-indolyl)-2-ethoxy-N-(2-pyrazinyl)-2,4-pentadienamide | 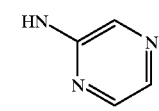 | | Me | —H | —H |
| 91 | (2Z,4E)-5-(5,6-Dichloro-2-indolyl)-2-methoxy-N-(6-pyrimidinyl)-2,4-pentadienamide | 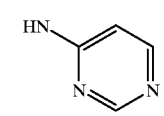 | | Me | —H | —H |
| 92 | (2Z,4E)-N-[2-(Aminomethyl)pyridyl]-5-(5,6-Dichloro-2-indolyl)-2-methoxy-2,4-pentadienamide | 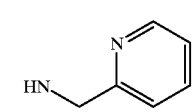 | | Me | —H | —H |
| 93 | (2Z,4E)-5-(5,6-Dichloro-2-indolyl)-2-methoxy-N-[4-methoxyphenyl)-2,4-pentadienamide | 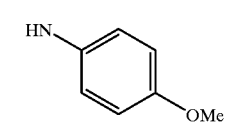 | | Me | —H | —H |
| 94 | (2Z,4E)-5-(5,6-Dichloro-2-indolyl)-2-methoxy-N-(3-quinolyl)-2,4-pentadienamide | 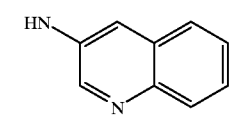 | | Me | —H | —H |
| 95 | (2Z,4E)-5-(5,6-Dichloro-2-indolyl)-2-methoxy-N-[3-(2,6-dimethoxy)pyridyl]-2,4-pentadienamide | 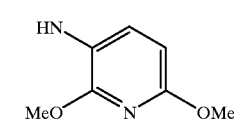 | | Me | —H | —H |
| 96 | (2Z,4E)-5-(5,6-Dichloro-2-indolyl))-2-methoxy-N-[4-(2-methoxy)pyridyl]-2,4-pentadienamide | 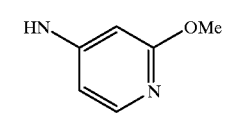 | | Me | —H | —H |

-continued

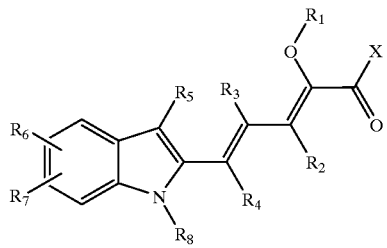

| | | | | | |
|---|---|---|---|---|---|
| 97 | (2Z,4E)-5-(5,6-Dichloro-2-indolyl)-2-methoxy-N-[3-[1-(2(R)-methyl)piperidinyl]-propyl]-2,4-pentadienamide | 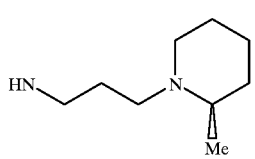 | Me | —H | —H |
| 98 | (2Z,4E)-5-(5,6-Dichloro-2-indolyl))-2-methoxy-N-[3-(2-methoxy)pyridyl]-2,4-pentadienamide | 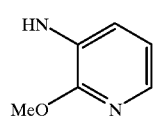 | Me | —H | —H |
| 99 | (2Z,4E)-5-(5,6-Dichloro-2-indolyl))-2-methoxy-N-[3-(6-phenoxy)pyridyl]-2,4-pentadienamide | 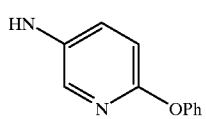 | Me | —H | —H |
| 100 | (2Z,4E)-5-(5,6-Dichloro-2-indolyl)-2-methoxy-N-[3-[1-(2(S)-methyl)piperidinyl]-propyl]-2,4-pentadienamide | 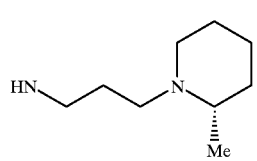 | Me | —H | —H |
| 101 | (2Z,4E)-5-(5,6-Dichloro-2-indolyl))-2-methoxy-N-[3-(2-methoxy-6-bromo)pyridyl]-2,4-pentadienamide | 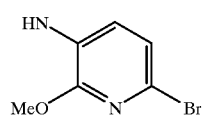 | Me | —H | —H |
| 102 | (2Z,4E)-5-(5,6-Dichloro-2-indolyl))-2-methoxy-N-[3-(6-morpholino)pyridyl]-2,4-pentadienamide | 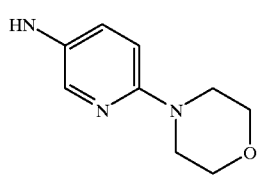 | Me | —H | —H |
| 103 | (2Z,4E)-5-(5,6-Dichloro-2-indolyl)-2-methoxy-N-[3-(1-ethyl)-piperidinyl]-2,4-pentadienamide | 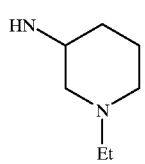 | Me | —H | —H |

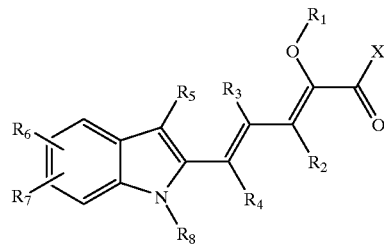

| 104 | (2Z,4E)-5-(5,6-Dichloro-2-indolyl)-N-[3-(cyclohexylamino)-propyl]-2-methoxy-2,4-pentadienamide | 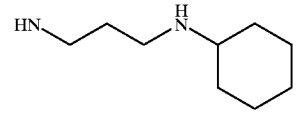 | Me | —H | —H |

| Ex. No. | R4 | R5 | R6 | R7 | R8 | M.P. (° C.) | N.M.R. |
|---|---|---|---|---|---|---|---|
| 13 | —H | —H | 5-Cl | —H | —H | 201 | $^1$H-NMR(DMSO-$d_6$): 3.75(s, 3H); 4.37(d, 2H); 6.56(s, 1H); 6.71(d, 1H); 6.87(d, 1H); 7.07–7.36(m, 8H); 7.53(s, 1H); 8.74 (t, 1H); 11.65(broad band, 1H). |
| 14 | —H | —H | 5-Cl | —H | —H | 185 | $^1$H-NMR(DMSO-$d_6$): 2.73(t, 2H); 3.36(td, 2H); 3.67(s, 3H); 3.70(s, 3H); 3.73(s, 3H); 6.55(s, 1H); 6.64(d, 1H); 6.70–6.88 (m, 4H); 7.10(m, 2H); 7.33(d, 1H); 7.53 (d, 1H); 8.16(t, 1H); 11.64(broad band, 1H). |
| 15 | —H | —H | 5-Cl | —H | —H | 228 | $^1$H-NMR(DMSO-$d_6$): 3.74(s, 3H); 4.39(d, 2H); 6.56(s, 1H); 6.71(d, 1H); 6.87(d, 1H); 7.12(dd, 1H); 7.18(dd, 1H); 7.35 (2d, 2H); 7.58(d, 1H); 7.68(dd, 1H); 8.49 (dd, 1H); 8.56(d, 1H); 8.81(t, 1H); 11.65 (broad band, 1H). |
| 16 | —H | —H | 5-Cl | —H | —H | 190 | $^1$H-NMR(DMSO-$d_6$): 3.72(s, 3H); 3.73(s, 3H); 3.74(s, 3H); 4.30(d, 2H); 6.55(s, 1H); 6.69(d, 1H); 6.77–6.92(m, 4H); 7.23 (m, 2H); 7.33(d, 1H); 8.65(t, 1H); 11.64 (broad band, 1H). |
| 17 | —H | —H | 5-Cl | —H | —H | 218 | $^1$H-NMR(DMSO-$d_6$): 3.71(s, 6H); 3.75(s, 3H); 4.30(d, 2H); 6.37(d, 1H); 6.45(d, 2H); 6.56(s, 1H); 6.71(d, 1H); 6.87(d, 1H); 7.19(m, 2H); 7.34(d, 1H); 7.54(d, 1H); 8.71(t, 1H); 11.67(broad band, 1H). |
| 18 | —H | —H | 5-F | —H | —H | 146 | $^1$H-NMR(DMSO-$d_6$): 3.73(s, 3H); 3.75(s, 3H); 6.60(s, 1H); 6.87–7.35(m, 6H); 11.62(broad band, 1H). |
| 19 | —H | —H | 5-NO$_2$ | —H | —H | 260 | $^1$H-NMR(DMSO-$d_6$): 3.75(s, 3H); 3.77(s, 3H); 6.88(s, 1H); 6.91(d, 1H); 7.06(d, 1H); 7.25(dd, 1H); 7.50(d, 1H); 8.02(dd, 1H); 8.50(d, 1H); 12.25(broad band, 1H). |
| 20 | —H | —H | 5-Cl | —H | —H | 45 (dec) | $^1$H-NMR(DMSO-$d_6$): 2.60–2.95(broad band, 1H); 3.25–3.80(m, 6H); 3.73(s, 3H); 4.77 (m, 2H); 6.06(d, 1H); 6.49(d, 1H); 6.55 (d, 1H); 6.93(dd, 1H); 7.05–7.60(m, 8H); 8.29(broad band, 1H). |
| 21 | —H | —H | 5-Cl | —H | —H | 226 | $^1$H-NMR(DMSO-$d_6$): 3.81(s, 3H); 6.59(s, 1H); 6.81(d, 1H); 6.93(d, 1H); 7.05–7.37 (m, 6H); 7.55(d, 1H); 7.77(d, 2H)p; 9.94 (broad band, 1H); 11.70 (broad band, 1H). |
| 22 | —H | —H | 5-sBu | —H | —H | 138 | $^1$H-NMR(DMSO-$d_6$): 0.83(t, 3H); 1.28(d, 3H); 1.59(m, 2H); 2.64(m, 1H); 3.81(s, 3H); 3.82(s, 3H); 6.59(d, 1H); 6.70–7.00 (m, 3H); 7.06(dd, 1H); 7.27(d, 1H); 7.36 (d, 1H); 8.23(broad band, 1H). |

-continued

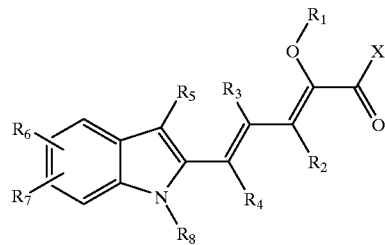

| | R1 | R2 | R5 | R6 | R7 | m.p. (°C) | NMR |
|---|---|---|---|---|---|---|---|
| 23 | —H | —H | 5-Cl | —H | —H | 235 | ¹H-NMR(DMSO-$d_6$): 3.73(s, 3H); 6.58 (s, 1H); 6.84(3, 1H); 6.94(d, 1H); 7.05–7.30(m, 2H); 7.34(d, 1H); 7.54(d, 1H); 11.69(broad band, 1H); 12.30–13.20 (broad band, 1H). |
| 24 | —H | —H | 5-Cl | —H | —H | 163 | ¹H-NMR(DMSO-$d_6$): 1.45(2m, 4H); 3.18 (td, 2H); 3.41(td, 2H); 3.71(s, 3H); 4.41 (t, 1H); 6.55(s, 1H); 6.58(d, 1H); 6.84(d, 1H); 7.00–7.25(m, 2H); 7.33(d, 1H); 7.53 (d, 1H); 8.16(t, 1H); 11.64(broad band, 1H). |
| 25 | —H | —H | 5-Cl | —H | —H | 189 | ¹H-NMR(DMSO-$d_6$): 1.12(t, 6H); 3.36(m, 4H); 3.62(s, 3H); 5.70(d, 1H); 6.45(s, 1H); 6.62(d, 1H); 7.00–7.25(m, 2H); 7.29 (d, 1H); 7.48(d, 1H); 11.54(broad band, 1H). |
| 26 | —H | —H | 5-Cl | —H | —H | 178 | ¹H-NMR(DMSO-$d_6$): 0.96(t, 6H); 1.59(m, 2H); 2.30–2.55(m, 6H); 3.10–3.35(m, 2H); 3.72(s, 3H); 6.55(s, 1H); 6.66(d, 1H); 6.85(d, 1H); 7.00–7.25(m, 2H); 7.34(d, 1H); 7.53(d, 1H); 8.31(t, 1H); 11.64 (broad band, 1H). |
| 27 | —H | —H | 5-Cl | —H | —H | 231 | ¹H-NMR(DMSO-$d_6$): 1.07(t, 3H); 3.19(td, 2H); 3.72(s, 3H); 6.55(s, 1H); 6.65(d, 1H); 6.84(d, 1H); 7.00–7.25(m, 2H); 7.33 (d, 1H); 7.53(d, 1H); 7.57(broad band, 1H); 11.65(broad band, 1H). |
| 28 | —H | —H | 5-Cl | —H | —H | 214 | ¹H-NMR(DMSO-$d_6$): 3.72(s, 3H); 6.55(s, 1H); 6.67(d, 1H); 6.83(d, 1H); 7.05–7.25 (m, 2H); 7.34(d, 1H); 7.34(broad band, 1H); 7.53(d, 1H); 7.57(broad band, 1H); 11.65(broad band, 1H). |
| 29 | —H | —H | 5-Cl | —H | —H | 113 | ¹H-NMR(DMSO-$d_6$): 3.25(s, 6H); 3.45–3.70(m, 8H); 3.63(s, 3H); 5.73(d, 1H); 6.45(s, 1H); 6.62(d, 1H); 7.05–7.25(m, 2H); 7.29(d, 1H); 7.49(d, 1H); 11.55 (broad band, 1H). |
| 30 | —H | —H | 5-Cl | —H | —H | 104–106 | ¹H-NMR(acetone-$d_6$):10.75(s br, 1H); 7.55(d, 1H); 7.35(d, 1H); 7.23(dd, 1H); 7.10(dd, 1H); 6.97(d, 1H); 6.91(d, 1H); 6.64(s, 1H); 4.23(q, 2H); 4.01(q, 2H); 1.31(t, 3H); 1.30(t, 3H). |
| 31 | —H | —H | 5-Cl | 7-Cl | —H | 196 | ¹H-NMR(DMSO-$d_6$): 3.74(s, 3H); 3.75(s, 3H); 6.74(s, 1H); 6.88(d, 1H); 6.99(d, 1H); 7.27(d, 1H); 7.48(dd, 1H); 7.57(d, 1H); 11.86(broad band, 1H). |
| 32 | —H | —H | 6-Cl | 7-Cl | —H | 190 | ¹H-NMR(DMSO-$d_6$): 3.74(s, 3H); 3.76(s, 3H); 6.78(s, 1H); 6.88(d, 1H); 6.99(d, 1H); 7.19(d, 1H); 7.50(d, 1H); 7.48(dd, 1H); 11.80(broad band, 1H). |
| 33 | —H | —H | 5-Cl | —H | —H | 257 | ¹H-NMR(DMSO-$d_6$): 3.84(s, 3H); 6.61(s, 1H); 6.87(d, 1H); 6.97(d, 1H); 7.11(dd, 1H); 7.15–7.45(m, 3H); 7.55(d, 1H); 8.19 (m, 1H); 8.30(m, 1H); 8.95(d, 1H); 10.19 (broad band, 1H); 11.71(broad band, 1H). |

-continued

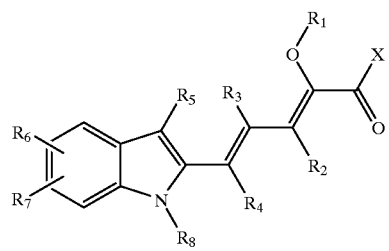

| # | R1 | R2 | R5 | R6 | R7 | mp (°C) | 1H-NMR |
|---|----|----|----|----|----|---------|--------|
| 34 | —H | —H | 5-Cl | 6-Cl | —H | 176 | 1H-NMR(DMSO-d6): 11.70(s, 1H); 8.27 (t, 1H); 7.74(s, 1H); 7.51(s, 1H); 7.16 (dd, 1H); 6.84(d, 1H); 6.63(d, 1H); 6.58 (s, 1H); 3.73(s, 3H); 3.20(dt, 2H); 2.45 (q, 4H); 2.41(t, 2H); 1.59(m, 2H); 0.96(t, 6H). |
| 35 | —H | 5-MeOPh | 5-OMe | 6-OMe | —H | 92–95 | 1H-NMR(CDCl3): 3.80(s, 3H); 3.85–4.05 (4s, 12H); 6.80–7.10(m, 7H); 7.35–7.50 (m, 2H); 8.28(broad band, 1H). |
| 36 | —H | —H | 5-Cl | 7-Me | —H | 166–168 | 1H-NMR(DMSO-d6): 2.50(s, 3H); 3.73 (s, 3H); 3.76(s, 3H); 6.62(s, 1H); 6.89(d, 1H); 6.94(d, 2H); 6.98(d, 1H); 7.37(d, 1H); 7.35(dd, 1H); 11.34(broad band, 1H. |
| 37 | —H | —H | 5-Cl | —H | —H | 187 | 1H-NMR(DMSO-d6): 3.72(s, 3H); 4.19 (d, 2H); 4.95(broad band, 2H); 6.50(d, 2H); 6.55(s, 1H); 6.68(d, 1H); 6.85(d, 1H); 6.95(d, 2H); 7.05–7.25(m, 2H); 7.33 (d, 1H); 7.53(d, 1H); 8.50(t, 1H); 11.64 (broad band, 1H) |
| 38 | —H | —H | 5-Cl | —H | —H | 110–112 | 1H-NMR(DMSO-d6): 1.17(t, 6H); 2.57(m, 2H); 3.72(s, 3H); 3.60–3.80(2H); 4.13 (2q, 4H); 5.40–5.65(m, 2H); 6.35(broad band, 1H); 6.56(s, 1H); 6.66(d, 1H); 6.85 (d, 1H); 7.05–7.40(m, 3H); 7.53(d, 2H); 9.25(broad band, 1H); 11.65(broad band, 1H). |
| 39 | —H | —H | 5-Cl | —H | —H | 146 | 1H-NMR(CDCl3): 1.33(t, 12H); 1.75–2.50 (m, 5H); 3.39(td, 2H); 3.79(s, 3H); 4.10–4.30(m, 8H); 6.57(s, 1H); 6.65–7.00(m, 4H); 7.13(dd, 1H); 7.26(d, 1H); 7.52(d, 1H); 8.89(broad band, 1H). |
| 40 | —H | —H | 5-Cl | —H | —H | 125 | 1H-NMR(DMSO-d6): 1.49(m, 4H); 1.80 (m, 2H); 3.16(m, 2H); 3.70(m, 15H); 4.60 (m, 1H); 6.55(s, 1H); 6.64(d, 1H); 6.84 (d, 1H); 7.15(mn, 2H); 7.35(d, 1H); 7.54 (d, 1H); 8.16(t, 1H); 11.64(broad band, 1H). |
| 41 | —H | —H | 5-OMe | 6-OMe | —H | 148–150 | 1H-NMR (benzene-d6): 7.21(s br, 1H); 7.03(d, 1H); 6.94(dd, 1H); 6.89(s, 1H); 6.48(d, 1H); 6.40(d, 1H); 6.36(s, 1H); 3.73(s, 3H); 3.59(s, 3H); 3.55(s, 3H); 3.48(s, 3H). |
| 42 | —H | —H | 5-Cl | 6-Cl | —H | 244–245 | 1H-NMR(DMSO-d6): 11.34(s br, 1H); 8.18 (s, 1H); 8.01(s, 1H); 7.69(dd, 1H); 7.44 (d, 1H); 7.37(d, 1H); 7.13(s, 1H); 4.25(s, 3H). |
| 43 | —H | —H | 5-Cl | 6-Cl | —H | 125 | 1H-NMR(DMSO-d6): 1.57(m, 2H); 2.65(t, 2H); 3.23(td, 2H), 3.46(s, 4H), 3.61(s, 6H); 3.72(s, 3H); 6.58(s, 1H); 6.64(d, 1H); 6.85(d, 1H); 7.17(dd, 1H); 7.52(s, 1H); 7.75(s, 1H); 8.17(t, 1H); 11.75(s, broad band, 1H) |

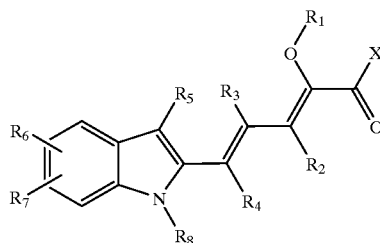

| | | | | | | |
|---|---|---|---|---|---|---|
| 44 | —H | —H | 5-Cl | 6-Cl | —H | 247–248 | $^1$H-NMR(DMSO-$d_6$): 3.85(s, 3H); 6.62(s, 1H); 6.85(d, 1H); 6.79(d, 1H); 7.25(dd, 1H); 7.37(dd, 1H); 7.54(s, 1H); 7.77(s, 1H); 8.18(ddd, 1H); 8.31(dd, 1H); 8.94 (d, 1H); 10.16(s br, 1H); 11.78(s br, 1H) |
| 45 | —H | —H | 5-Cl | 6-Cl | —H | 228 | $^1$H-NMR(DMSO-$d_6$): 1.58(m, 2H); 2.66(t, 2H); 3.21(td, 2H); 2.80–4.00(broad band, 2H); 3.34(s, 4H); 3.72(s, 3H); 6.58(s, 1H); 6.64(d, 1H); 6.85(d, 1H); 7.17(dd, 1H); 7.51(s, 1H); 7.75(s, 1H); 8.21(t, 1H); 11.75(s, broad band, 1H) |
| 46 | —H | —H | 5-Cl | 6-Cl | —H | 162–164 | $^1$H-NMR(DMSO-$d_6$+TFA): 1.20(t, 1H); 3.20(m, 6H); 3.52(dt, 1H); 3.76(s, 3H); 6.61(s br, 1H); 6.76(d, 1H); 6.90(d, 1H); 7.20(dd, 1H); 7.54(s br, 1H), 7.75(s, 1H); 8.40(t, 1H); 9.25(s, br, 1H); 11.75(s br, 1H) |
| 47 | —H | —H | 5-Cl | 6-Cl | —H | 280 | $^1$H-NMR(DMSO-$d_6$): 1.19(t, 3H); 2.88(m, 2H); 1.72(m, 2H); 2.86(m, 2H); 3.71(s, 3H); 3.87(m, 1H); 3.93(m, 2H); 4.04(q, 2H); 6.58(s, 1H); 6.64(d, 1H); 6.86(d, 1H); 7.17(dd, 1H); 7.52(s, 1H); 7.75(s, 1H); 8.04(d, 1H); 11.75(s, broad band, 1H) |
| 48 | —H | —H | 5-Cl | 6-Cl | —H | 256 | $^1$H-NMR(DMSO-$d_6$): 3.86(s, 3H); 6.64(s, 1H); 6.91(d,m 1H); 6.97(d, 1H); 7.17(m, 1H); 7.26(dd, 1H); 7.54(s, 1H); 7.77(s, 1H); 7.85(m, 1H); 8.14(d, 1H); 8.37(m, 1H); 9.84(s, broad band, 1H); 11.81(s, broad band, 1H) |
| 49 | —H | —H | 5-Cl | 6-Cl | —H | 178 | $^1$H-NMR(DMSO-$d_6$): 1.90(m, 2H); 3.13 td, 2H), 3.70(s, 3H); 3.96(t, 2H); 6.61(s, 1H); 6.66(d, 1H); 6.84(d, 1H); 6.88(s, 1H); 7.13(dd, 1H); 7.19(s, 1H); 7.54(s, 1H); 7.66(s, 1H); 7.73(s, 1H); 8.33(t, 1H); 11.77(s, broad band, 1H) |
| 50 | —H | —H | 5-Cl | 6-Cl | —H | 252 | $^1$H-NMR(DMSO-$d_6$): 1.30(m, 1H); 1.43–1.86(m, 4H); 2.57–2.78(m, 4H); 2.78–3.13(m, 2H); 3.73(s, 3H)(; 3.83(m, 1H); 6.57(s, 1H); 6.58(d, 1H); 6.85(d, 1H); 7.19(dd, 1H); 7.53(s, 1H); 7.75(s, 1H); 8.06(d, 1H); 11.77(s, broad band, 1H) [α]$_D^{20}$=–25 c=1 MeOH |
| 51 | —H | —H | 5-Cl | 6-Cl | —H | 186–187 | $^1$H-NMR(DMSO-$d_6$): 1.63(m, 2H); 2.36–2.28(m, 6H); 3.21(dt, 2H); 3.58(dd, 4H); 3.73(s, 3H); 6.58(s, 1H); 6.64(d, 1H); 6.85(d, 1H); 7.17(dd 1H); 7.52(s, 1H); 7.74(s, 1H); 8.20(t, 1H); 10.70(s br, 1H) |
| 52 | —H | —H | 5-Cl | 6-Cl | —H | 90 | $^1$H-NMR(DMSO-$d_6$): 0.94(t, 6H); 1.10(d, 3H); 1.42(m, 4H); 2.28–2.55(m, 6H); 3.71 (s, 3H); 3.90(m, 1H); 6.57(s, 1H); 6.61 (d, 1H); 6.83(d, 1H); 7.18(dd, 1H); 7.51 (s, 1H); 7.75(s, 1H); 7.90(d, 1H); 11.75 (s, broad band, 1H) |

-continued

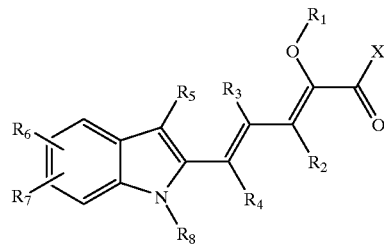

| | R1 | R2 | R5 | R6 | R7 | m.p.(°C) | |
|---|---|---|---|---|---|---|---|
| 53 | —H | —H | 5-Cl | 6-Cl | —H | 250 | ¹H-NMR(DMSO-$d_6$): 1.26–1.82(m, 6H); 2.56–3.12(m, 6H); 3.45(td, 2H); 3.76(s, 3H); 6.59(s, 1H); 6.71(d, 1H); 6.88(d, 1H); 7.20(dd, 1H); 7.53(s, 1H); 7.76(s, 1H); 8.33(s, broad band, 1H); 11.84(s, broad band, 1H) |
| 54 | —H | —H | 5-Cl | 6-Cl | —H | 230 | ¹H-NMR(DMSO-$d_6$): 1.39–2.20(m, 6H); 2.46(s, 3H); 2.35–2.67(m, 2H); 3.16(s, 1H); 3.23(td, 2H); 3.73(s, 3H); 6.58(s, 1H); 6.67(d, 1H); 6.86(d, 1H); 7.19(dd, 1H); 7.53(s, 1H); 7.76(s, 1h); 8.32(t, 1H); 11.82(s, broad band, 1H) |
| 55 | —H | —H | 5-Cl | 6-Cl | —H | 252 | ¹H-NMR(DMSO-$d_6$): 3.22(t, 2H); 3.59(t, 2H); 3.73(s, 3H); 6.59(s, 1H); 6.82(d, 1H); 6.94(d, 1H); 7.22(dd, 1H); 7.51(s, 1H); 7.75(s, 1H); 9.40(s, broad band, 1H); 11.76(s, broad band, 1H) |
| 56 | —H | —H | 5-Cl | 6-Cl | —H | 225 | ¹H-NMR(DMSO-$d_6$): 1.39(d, 12H); 1.59 (m, 2H); 1.83(m, 2H); 3.72(s, 3H); 4.23 (m, 1H); 6.58(s, 1H); 6.63(d, 1H); 6.86 (d, 1H); 7.19(dd, 1H); 7.53(s, 1H); 7.73 (s, 1H); 8.24(d, 1H); 11.83(s, broad band, 1H) |
| 57 | —H | —H | 5-Cl | 6-Cl | —H | 281 | ¹H-NMR(DMSO-$d_6$): 3.82(s, 3H); 3.83(s, 3H); 6.63(s, 1H); 6.83(2d, 2H); 6.95(d, 1H); 7.25(dd, 1H); 7.54(s, 1H); 7.77(s, 1H); 8.04(dd, 1H); 8.52(d, 1H); 10.05(s, 1H); 11.81(s, broad band, 1H) |
| 58 | —H | —H | 5-Cl | 6-Cl | —H | 98 | ¹H-NMR(DMSO-$d_6$): 0.95(t, 6H); 1.76(m, 2H); 2.45(m, 6H); 3.73(s, 3H); 4.20t, 2H); 6.63(s, 1H); 6.88(d, 1H); 6.99(s, 1H); 7.21(dd, 1H); 7.53(s, 1H); 7.77(s, 1H); 11.82(s, broad band, 1H) |
| 59 | —H | —H | 5-Cl | 6-Cl | —H | 184 | ¹H-NMR(DMSO-$d_6$): 0.9(d, 3H); 1.09–1.72(m, 8H); 1.99(m, 1H); 2.21(m, 2H); 2.57–2.88(m, 2H); 3.18(td, 2H); 3.73(s, 3H); 6.58(s, 1H); 6.64(d, 1H); 6.85(s, 1H); 7.17(dd, 1H); 7.52(s, 1H); 7.75(s, 1H); 8.39(t, 1H); 11.75(s, broad band, 1H) |
| 60 | —H | —H | 5-Cl | 6-Cl | —H | 263 | ¹H-NMR(DMSO-$d_6$): 2.17(s, 3H); 2.39 (m, 4H); 2.82(t, broad band, 4H); 3.70(s, 3H); 6.53(d, 1H); 6.57(s, 1H); 6.84(d, 1H); 7.16(dd, 1H); 7.51(s, 1H); 7.74(s, 1H); 9.15(s, 1H); 11.75(s, broad band, 1H) |
| 61 | —H | —H | 6-Cl | —H | —H | 179 | ¹H-NMR(DMSO-$d_6$): 3.73(s, 3H); 3.75(s, 3H); 6.64(s, 1H); 6.90(d, 1H); 6.99(d, dd, 2H); 7.18(dd, 1H); 7.34(d, 1H); 7.52(d, 1H); 11.68(s, broad band, 1H) |
| 62 | —H | —H | 5-Cl | 6-Cl | —H | 120 | ¹H-NMR(DMSO-$d_6$): 1.00(t, 3H); 1.66(m, 2H); 2.46(m, 4H); 3.18(td, 2H); 3.55(s, borad band, 2H); 3.67(s, 3H); 6.58(s, 1H); 6.63(d, 1H); 6.84(d, 1H); 7.17(dd, 1H); 7.32(m, 5H); 7.52(s, 1H); 7.75(s, 1H); 8.16(t, 1H); 11.76(s, broad band, 1H) |

-continued

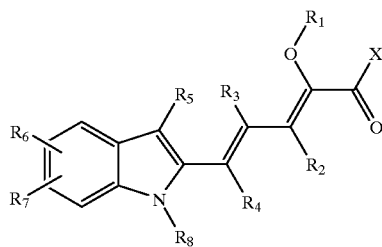

| | | | | | | |
|---|---|---|---|---|---|---|
| 63 | —H | —H | 5-Cl | 6-Cl | —H | 237 | $^1$H-NMR(DMSO-$d_6$): 1.15–1.88(m, 5H); 2.56–2.76(m, 4H); 2.77–3.11(m, 2H); 3.73(s, 3H); 3.82(m, 1H); 6.57(s, 1H); 6.58(d, 1H); 6.84(d, 1H); 7.18(dd, 1H); 7.51(s, 1H); 7.75(s, 1H); 8.02(d, broad band, 1H); 11.76(s, broad band, 1H) |
| 64 | —H | —H | 5-Cl | 6-Cl | —H | 188–189 | $^1$H-NMR(DMSO-$d_6$):0.86(s, 6H); 2.19(s, 2H); 2.27(s, 6H); 3.11(d, 2H); 3.76(s, 3H); 6.59(s, 1H); 6.67(d, 1H); 6.87(d, 1H); 7.18(dd, 1H); 7.52(s, 1H); 7.75(s, 1H); 8.50(t, broad band, 1H); 11.76(s, broad band, 1H) |
| 65 | —H | —H | 5-Cl | 6-Cl | —H | 204 | $^1$H-NMR(DMSO-$d_6$): 3.73(s, 3H); 6.60(s, 1H); 6.84(d, 1H); 6.95(d, 1H); 7.19(dd, 1H); 7.51(d, 1H); 7.52(s, 1H); 7.76(s, 1H): 8.53(dd, 1H); 8.76(dd, 1H); 11.79 (s, broad band, 1H) |
| 66 | —H | —H | 5-Cl | 6-Cl | —H | 260 | $^1$H-NMR(DMSO-$d_6$): 1.55–1.93(m, 6H); 1.94–2.17(m, 2H); 2.42(s, broad band, 3H); 3.39(m, 2H); 3.70(s, 3H); 4.07(m, 1H); 6.57(s, 1H); 6.61(d, 1H); 6.85(d, 1H); 7.17(dd, 1H); 7.52(s, 1H); 7.75(s, 1H); 8.03(d, broad band, 1H); 11.78(s, broad band, 1H) |
| 67 | —H | —H | 5-Cl | 6-Cl | —H | 179 | $^1$H-NMR(DMSO-$d_6$): 1.61 m, 2H); 2.15(s, 3H); 2.19–2.45(m, 10H); 3.19(td, 2H); 3.73(s, 3H); 6.58(s, 1H); 6.64(d, 1H); 6.85(d, 1H); 7.18(dd, 1H); 7.52(s, 1H); 7.75(s, 1H); 8.24(t, 1H); 11.76(s, broad band, 1H) |
| 68 | —H | —H | 5-Cl | 6-Cl | —H | 280 | $^1$H-NMR(DMSO-$d_6$): 1.10(m, 2H); 1.61–1.93(m, 3H); 2.65–3.2(m, 4H); 3.63(s, 3H); 3.73(s, 3H); 3.86–4.40(m, broad band, 2H); 5.73(d, 1H); 6.47(s, 1H); 6.58 (s, 1H); 6.60–6.71(m, 2H); 6.86(d, 1H); 7.03–7.27(2dd, 2H); 7.47(s, 1H); 7.52(s, 1H); 7.70(s, 1H); 7.75(s, 1H); 8.23(t, 1H); 11.69(s, broad band, 1H); 11.75(s, broad band 1H) |
| 69 | —H | —H | 5-Cl | 6-Cl | —H | 232 | $^1$H-NMR(DMSO-$d_6$): 1.75(m, 2H); 2.50 (t, 2H); 2.66(t, 2H); 2.83(t, 2H); 3.26(td, 2H); 3.57(s, 2H); 3.59(s, 3H); 6.57(s, 1H); 6.63(d, 1H); 6.81(d, 1H); 7.01–7.23 (m, 5H); 7.51(s, 1H); 7.75(s, 1H); 8.37(t, 1H); 11.75(s, broad band, 1H) |
| 70 | —H | —H | 5-Cl | 6-Cl | —H | 235 | $^1$H-NMR(DMSO-$d_6$): 1.45–1.75(m, 4H), 1.90(m, 2H); 2.14(s, 3H); 2.73(m, 2H); 3.61(m, 1H); 3.71(s, 3H); 6.58(s, 1H); 6.60(d, 1H); 6.84(d, 1H); 7.17(dd, 1H); 7.51(s, 1H); 7.75(s, 1H); 7.96(d, 1H); 11.76(s, broad band, 1H) |
| 71 | —H | —H | 5-Cl | 6-Cl | —H | 295 | $^1$H-NMR(DMSO-$d_6$): 3.87(s, 3H); 6.68 (s, 1H); 6.93–7.13(2d, 2H); 7.30(dd, 1H); 7.55(s, 1H); 7.78(s, 1H); 8.44(s, 1H); 8.68(s, 1H); 10.72(broad band, 1H); 11.86(s, 1H); 13.93(broad band, 1H); 11.86(s, 1H); 13.93(broad band, 1H) |

-continued

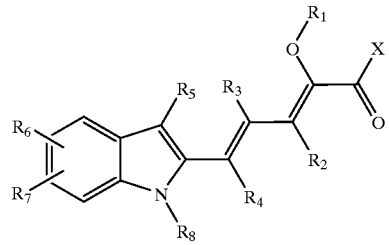

| | | | | | | |
|---|---|---|---|---|---|---|
| 72 | —H | —H | 5-Cl | 6-Cl | —H | 274 | ¹H-NMR(DMSO-d₆): 3.95(s, 3H); 6.64 (s, 1H); 6.90(d, 1H); 6.98(d, 1H); 7.31 (dd, 1H); 7.52–7.85(m, 3H), 7.55(s, 1H); 7.78(s, 1H); 7.96(d, 1H); 8.32(d, 1H); 6.94(dd, 1H); 10.31(s, broad band, 1H); 11.84(s, broad band, 1H) |
| 73 | —H | —H | 5-Cl | 6-Cl | —H | 278 | ¹H-NMR(DMSO-d₆): 3.83(s, 3H); 6.64 (s, 1H); 6.88(d, 1H); 6.98(d, 1H); 7.26 (dd, 1H); 7.51(d, 1H); 7.54(s, 1H); 7.77 (s, 1H); 8.26(dd, 1H); 8.81(d, 1H); 10.34 (s, 1H); 11.82(s, broad band, 1H) |
| 74 | —H | —H | 5-Cl | 6-Cl | —H | 199 | ¹H-NMR(DMSO-d₆): 1.18(t, 6H); 3.76(s, 3H); 4.16(q, 4H); 4.37(d, 2H); 6.59(s, 1H); 6.70(d, 1H); 6.87(d, 1H); 7.14(s, 1H); 7.19(dd, 1H); 7.26(d, broad band, 2H); 7.44(d, broad band, 2H); 7.53(s, 1H); 7.75(s, 1H); 8.78(t, 1H); 11.78(s, broad band, 1H) |
| 75 | —H | —H | 5-Cl | 6-Cl | —H | 275 | ¹H-NMR(DMSO-d₆): 2.86(s, 6H); 3.81 (s, 3H); 6.60(s, 1H); 6.7(d, 2H); 6.76(d, 1H); 6.89(d, 1H); 7.24(dd, 1H); 7.53(s, 1H); 7.58(d, broad band, 2H); 7.76(s, 1H); 9.72(s, 1H); 11.78(s, broad band, 1H) |
| 76 | —H | —H | 5-Cl | 6-Cl | —H | >250 | ¹H-NMR(DMSO-d₆): 3.55–3.30(m, 16H); 3.60(s, 3H); 4.59(s br, 1H); 5.76(d, 1H); 6.48(s br, 1H); 6.65(d, 1H); 7.11(dd, 1H); 7.49(s, 1H); 7.70(s, 1H); 11.63(s br, 1H) |
| 77 | —H | —H | 5-Cl | 6-Cl | —H | >250 | ¹H-NMR(DMSO-d₆): 1.40(m, 2H); 1.58 (m, 2H); 1.71(m, 2H); 2.40–220(m, 6H); 3.60–3.30(m, 10H); 3.62(s, 3H); 4.39(t, 1H); 5.68(d, 1H) 6.47(s br, 1H); 6.61(d, 1H); 7.11(dd, 1H); 7.47(s, 1H); 7.70(s, 1H); 11.58(s br, 1H) |
| 78 | —H | —H | 5-Cl | 6-Cl | —H | Deliquescent | ¹H-NMR(DMSO-d₆): 0.92(s br, 6H); 1.66 (m, 2H); 2.50–2.30(m, 6H); 2.98(s br, 3H); 3.38(dd, 2H); 3.62(s, 3H); 5.72(d, 1H); 6.46(s br, 1H); 6.61(d, 1H); 7.14 (dd, 1H); 7.48(s, 1H); 7.70(s, 1H); 11.60 (s br, 1H) |
| 79 | —H | —H | 5-Cl | 6-Cl | —H | 234 | ¹H-NMR(DMSO-d₆): 0.97(d, broad band, 6H); 2.03–2.77(m, 4H); 3.62(s, 3H); 3.51– 3.95(m, broad band, 1H); 3.95–4.40(m, borad band, 1H); 5.74(d, 1H); 6.47(s, 1H); 6.63(d, 1H); 7.13(dd, 1H); 7.48(s, 1H); 7.71(s, 1H); 11.67(s, broad band, 1H) |
| 80 | —H | —H | 5-Cl | 6-Cl | —H | 244 | ¹H-NMR(DMSO-d₆): 3.81(s, 3H); 6.73 (m, 1H + 2H exch. with D₂O): 6.97(d, 1H); 7.10(d, 1H); 7.35(dd, 1H); 7.56(s, 1H); 7.80(s, 1H); 8.92(s, 1H); 8.97(s, 1H); 11.92(s, broad band, 1H) |

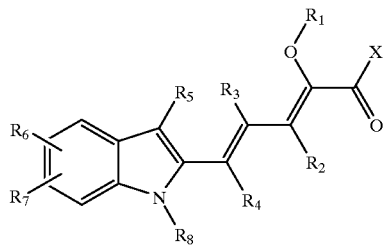

| | | | | | | | |
|---|---|---|---|---|---|---|---|
| 81 | —H | —H | 5-Cl | 6-Cl | —H | 229 | ¹H-NMR(DMSO-d₆): 2.96(t, 2H); 3.53 (td, 2H); 3.68(s, 3H); 6.58(s, 1H); 6.64 (d, 1H); 6.85(d, 1H); 7.16(dd, 1H); 7.18–7.31(m, 2H); 7.52(s, 1H); 7.69(dd, 1H); 7.75(s, 1H); 8.27(t, 1H); 8.51(m, 1H); 11.76(s, broad band, 1H) |
| 82 | —H | —H | 5-Cl | 6-Cl | —H | 176 | ¹H-NMR(DMSO-d₆): 373(s, 3H); 3.82 (s, 3H); 4.30(d, 2H); 6.59(s, 1H); 6.69(d, 1H); 6.78(d, 1H); 6.87(d, 1H); 7.18(dd, 1H); 7.52(s, 1H); 7.64(dd, 1H); 7.75(s, 1H); 8.09(d, 1H); 8.74(t, 1H); 11.76(s, broad band, 1H) |
| 83 | —H | —H | 5-Cl | 6-Cl | —H | 164–166 | ¹H-NMR(DMSO-d₆): 0.96(d, 6H); 1.61 (m, 2H); 1.84(q, 2H); 1.96–2.36(m, 3H); 2.15(s, 3H); 2.58–2.88(m, 3H); 3.18(m, 2H); 3.73(s, 3H); 6.58(s, 1H); 6.64(d, 1H); 6.85(d, 1H); 7.18(dd, 1H); 7.52(s, 1H); 7.75(s, 1H); 8.25(t, 1H); 11.76(s, broad band, 1H) |
| 84 | —H | —H | 5-Cl | 6-Cl | —H | 223 | ¹H-NMR(DMSO-d₆): 1.68(m, 2H); 2.20–2.50(m, 6H); 3.23(td, 2H); 3.59–3.83(m, 7H); 6.51–6.64(m, 2H); 6.56(d, 1H); 6.85 (d, 1H); 7.18(dd, 1H); 7.51(s, 1H); 7.75 (s, 1H); 8.29(t, 1H); 8.35(m, 2H); 11.77 (s, broad band, 1H) |
| 85 | —H | —H | 5-Cl | 6-Cl | —Me | 171–172 | ¹H-NMR(CDCl₃): 3.70(s, 3H); 3.80(s, 3H); 3.82(s, 3H); 6.77(s br, 1H); 6.80(d, 1H); 6.89(dd, 1H); 7.23(dd, 1H); 7.37(s, 1H); 7.62(s, 1H) |
| 86 | —H | —H | 5-Cl | 6-Cl | —CH₂—COOtBut | 131–132 | ¹H-NMR(CDCl₃): 1.50(s, 9H); 3.85(s, 3H); 3.90(s, 3H); 4.75(s, 2H); 6.70(d, 1H); 6.85(s, 1H); 6.89(d, 1H); 7.25(dd, 1H); 7.34(s, 1H); 7.69(s, 1H) |
| 87 | —H | —H | 5-Cl | 6-Cl | —H | 193–195 | ¹H-NMR(DMSO-d₆): 0.98(s, 3H); 1.07 (s, 3H); 1.12(s, 3H); 1.14(s, 3H); 1.5(m, 1H); 1.73(m, 1H); 2.14(m, 1H); 3.15(td, 2H); 3.71(s, 3H); 6.58(s, 1H); 6.62(d, 1H); 6.84(d, 1H); 7.17(dd, 1H); 7.51(s, 1H); 7.75(s, 1H); 8.15(t, 1H); 11.75(s, broad band, 1H) |
| 88 | —H | —H | 5-Cl | 6-Cl | —H | 290–291 | ¹H-NMR(DMSO-d₆): 3.84(s, 3H); 4.00 (s, 3H); 6.64(s, 1H); 6.90(d, 1H); 6.96(d, 1H); 7.26(dd, 1H); 7.309d, 1H); 7.54(s, 1H); 7.77(s, 1H); 8.20(d, 1H); 10.53(s, broad band, 1H); 11.83(s, broad band, 1H) |
| 89 | —H | —Et | 5-Cl | 6-Cl | —H | 196–199 | ¹H-NMR(benzene-d₆): 0.95(t, 3H); 2.39 (q, 2H); 3.48(s, 3H); 3.70(s, 3H); 6.47(d, 1H); 6.76(s br, 1H)6.77(dd, 1H); 6.93 (d, 1H); 6.95(s, 1H); 7.53(s, 1H); |
| 90 | —H | —H | 5-Cl | 6-Cl | —H | 204 dec | ¹H-NMR(DMSO-d₆ + D₂O): 3.68(s, 3H); 6.62(s, 1H); 6.82(d, 1H); 6.91(d, 1H); 7.14(dd, 1H) 7.44–7.62(m, 1H); 7.54(s, 1H); 7.73(s, 1H); 8.47(d, 1H); 8.73(m, 1H) |

-continued

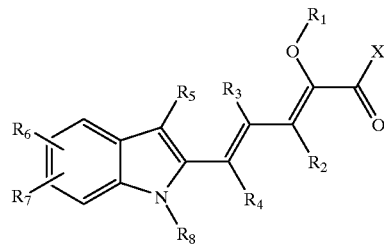

| | | | | | | |
|---|---|---|---|---|---|---|
| 91 | —H | —H | 5-Cl | 6-Cl | —H | 195 | ¹H-NMR(DMSO-d₆ + D₂O) (70° C.):3.72 (s, 3H); 6.62(s, 1H); 6.78(d, 1H); 6.88(d, 1H); 7.13(dd, 1H); 7.48(dd, 1H); 7.53(s, 1H); 7.70(s, 1H); 8.43(dd, 1H); 8.71(d, 1H) |
| 92 | —H | —H | 5-Cl | 6-Cl | —H | 216–218 | ¹H-NMR(DMSO-d₆): 3.80(s, 3H); 4.5(d, 2H); 6.59(s, 1H); 6.73(d, 1H); 6.88(d, 1H); 7.20(dd, 1H); 7.28(m, 2H); 7.51(s, 1H); 7.74(s, 1H); 7.75(ddd, 1H); 8.5(d, 1H); 8.70(t, 1H); 11.70(s, 1H) |
| 93 | —H | —H | 5-Cl | 6-Cl | —H | >250 | ¹H-NMR(DMSO-d₆): 3.72(s, 3H); 3.80 (s, 3H); 6.61(s, 1H); 6.77(d, 1H); 6.90(d, 2H); 6.92(d, 1H); 7.23(dd, 1H); 7.53(s, 1H); 7.67(d, 2H); 7.76(s, 1H); 9.81(s, 1H); 11.80(s, 1H) |
| 94 | —H | —H | 5-Cl | 6-Cl | —H | >250 | ¹H-NMR(DMSO-d₆): 3.84(s, 3H); 6.65 (s, 1H); 6.90(d, 1H); 6.99(d, 1H); 7.28 (dd, 1H); 7.53(s, 1H); 7.58(dd, 1H); 7.68 (dd, 1H); 7.77(s, 1H); 7.95(dd, 1H); 8.80 (d, 1H); 9.17(d, 1H); 10.40(s, 1H); 11.80 (s, 1H) |
| 95 | —H | —H | 5-Cl | 6-Cl | —H | 296 | ¹H-NMR(DMSO-d₆): 3.86(s, 6H); 3.94(s, 3H); 6.41(d, 1H); 6.62 s, 1H); 6.83(d, 1H); 6.95(d, 1H); 7.24(dd, 1H); 7.54(s, 1H); 7.77(s, 1H); 8.06(d, 1H); 9.02(s, 1H); 11.81(s, broad band, 1H). |
| 96 | —H | —H | 5-Cl | 6-Cl | —H | 276 | ¹H-NMR(DMSO-d₆): 3.80(s, 3H); 3.82(s, 3H); 6.63(s, 1H); 6.85(d, 1H); 6.97(d, 1H); 7.24(dd, 1H); 7.54(s, 1H); 7.77(s, 1H); 8.06(d, 1H); 9.02(s, 1H); 11.81(s, broad band, 1H). |
| 97 | —H | —H | 5-Cl | 6-Cl | —H | 170 | ¹H-NMR(DMSO-d₆): 0.99(d, 3H); 1.09–1.72(m, 8H); 1.99(m, 1H); 2.21(m, 2H); 2.57–2.88(m, 2H); 3.18(td, 2H); 3.73(s, 3H); 6.58(s, 1H); 6.64(d, 1H); 6.85(s, 1H); 7.17(dd, 1H); 7.52(s, 1H); 7.75(s, 1H); 8.29(t, 1H); 11.75(s, broad band, 1H) [α]_D^{20}=−23 (c=1, MeOH) |
| 98 | —H | —H | 5-Cl | 6-Cl | —H | 277 | ¹H-NMR(DMSO-d₆): 3.89 s, 3H); 3.97(s, 3H); 6.64(s, 1H); 6.90(d, 1H); 6.95–7.10 (m, 2H); 7.25(dd, 1H); 7.55(s, 1H); 7.78 (s, 1H); 7.94(dd, 1H); 8.36(dd, 1H); 9.05 (s, 1H); 11.84(s, broad band, 1H). |
| 99 | —H | —H | 5-Cl | 6-Cl | —H | 248–249 | ¹H-NMR(DMSO-d₆): 3.82(s, 3H); 6.63(s, 1H); 6.84(d, 1H); 6.95(d, 1H); 7.04(d, 1H); 7.11(dd, 2H); 7.19(ddd, 1H); 7.24 (dd, 1H); 7.41(dd, 2H); 7.54(s, 1H); 7.76 (s, 1H); 8.22(dd, 1H); 8.51(d, 1H); 10.13 (s, 1H); 11.77(s broad band, 1H). |
| 100 | — | — | 5-Cl | 6-Cl | —H | 171 | ¹H-NMR(DMSO-d₆): 0.99(d, 3H); 1.09–1.72(m, 8H); 1.99(m, 1H); 2.21(m, 2H); 2.57–2.88(m, 2H); 3.18(td, 2H); 3.73(s, 3H); 6.58(s, 1H); 6.64(d, 1H); 6.85(s, 1H); 7.17(dd, 1H); 7.52(s, 1H); 7.75(s, 1H); 8.29(t, 1H); 11.75(s, broad band, 1H) [α]_D^{20}=+29 (c=1, MeOH) |

-continued

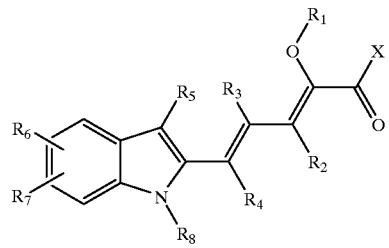

| | R1 | R2 | R3 | R4 | R5 | R6 | R7 | R8 | | 1H-NMR |
|---|---|---|---|---|---|---|---|---|---|---|
| 101 | —H | —H | 5-Cl | 6-Cl | —H | | | | 293 | 1H-NMR(DMSO-d6): 3.88(s, 3H); 3.96(s, 3H); 6.64(s, 1H); 6.90(d, 1H); 7.00(d, 1H); 7.24(dd, 1H); 7.27(d, 1H); 7.54(s, 1H); 7.77(s, 1H); 8.27(d, 1H)/ 9.08(s, 1H); 11.83 (s, broad band, 1H). |
| 102 | —H | —H | 5-Cl | 6-Cl | —H | | | | >250 | 1H-NMR(DMSO-d6): 3.39(m, 4H); 3.70 (m, 4H); 3.82(s, 3H); 6.62(s, 1H); 6.80 (d, 1H); 6.83(d, 1H); 6.92(d, 1H); 7.24 (dd, 1H); 7.53(s, 1H); 7.75(s, 1H); 7.92 (dd, 1H); 8.48(d, 1H); 9.87(s, 1H); 11.75 (s, 1H). |
| 103 | —H | —H | 5-Cl | 6-Cl | —H | | | | 166–167 | 1H-NMR(DMSO-d6): 0.99(t, 3H); 1.55–1.35(m, 2H); 1.65(m, 2H); 1.98(t br, 2H); 2.34(q, 2H); 2.74–2.55(m, 2H); 3.73 (s, 3H); 3.82(m, 1H); 6.58(s, 1H); 6.64 (d, 1H); 6.85(d, 1H); 7.17(dd, 1H); 7.52 (s, 1H); 7.74(s, 1H); 7.77(s broad band, 1H); 11.74(s, 1H). |
| 104 | —H | —H | 5-Cl | 6-Cl | —H | | | | >250 | 1H-NMR(DMSO-d6 + TFA): 1.35–1.20(m, 5H); 2.90–2.60(m, 5H); 3.00–2.90(m, 3H); 3.30(dt, 2H); 3.76(s, 3H); 6.60(s, 1H); 6.69(d, 1H); 6.89(d, 1H); 7.18(dd, 1H); 7.51(s, 1H); 7.75(s, 1H); 8.35(t, 1H); 8.43(s, broad band, 1H); 11.75(s, 1H). |

EXAMPLE 58

3-(Diethylamnino)propyl (2Z,4E)-5-(5,6-dichloro-2-indolyl)-2-methoxy-2,4-pentadienoate. A mixture of (2Z, 4E)-5-(5,6-dichloro-2-indolyl)-2-methoxy-2,4-pentadienoic acid (0.5 g, 1.6 mmol), 1-hydroxy-7-azabenzotriazole (0.22 g, 1.6 mmol), 3-diethylamino-1-propanol (0.23 g, 1.76 mmol) and 1-(3-dimethylaminopropyl)-3-ethylcarbodiimide hydrochloride (0.31 g, 1.6 mmol) in 50 ml of $CH_2Cl_2$ was refluxed for 1.5 h. After cooling, the reaction mixture was washed with water, dried over MgSO4 and concentrated under vacuum. The residue was purified by flash-chromatography ($CH_2Cl_2$/MeOH 9:1) and afforded after recrystallisation in a mixture of isopropyl ether/pentane 0.15 g (25%) of the title compound as yellow crystals, m.p.=98° C. 1H-NMR (DMSO-d6): 0.95 (t, 6H); 1.76 (m, 2H); 2.45 (m, 6H); 3.73 (s, 3H); 4.20 (t, 2H); 6.63 (s, 1H); 6.88 (d, 1H); 6.99 (s, 1H); 7.21 (dd, 1H); 7.53 (s, 1H); 7.77 (s, 1H); 11.82 (s, broad band, 1H)

Further Examples:

(a) The following compounds are prepared according to methods disclosed herein:

| Compound | X | R1 | R2 | R3 | R4 | R5 | R6 | R7 | R8 |
|---|---|---|---|---|---|---|---|---|---|
| Methyl (2Z,4E)-5-[2-(1-ydroxyindolyl)]-2-methoxy-2,4-pentadienoate | OMe | Me | H | H | H | H | H | H | OH |
| Methyl (2Z,4E)-5-(2-indolyl)-4-propyl-2-methoxy-2,4-pentadienoate | OMe | Me | H | H | Pr | H | H | H | H |

-continued

| Compound | X | $R_1$ | $R_2$ | $R_3$ | $R_4$ | $R_5$ | $R_6$ | $R_7$ | $R_8$ |
|---|---|---|---|---|---|---|---|---|---|
| Methyl (2Z,4E)-5-(2-indolyl)-2-methoxy-3-methyl-2,4-pentadienoate | OMe | Me | Me | H | H | H | H | H | H |
| Methyl (2Z,4E)-5-(3-indolyl)-2-methoxy-2,4-pentadienoate | OMe | Me | H | H | H | H | H | H | H |

LIST OF ABBREVIATIONS USED IN THE ABOVE PREPARATIONS AND EXAMPLES

| | |
|---|---|
| Celite | Registered trade mark for dicalite |
| DMF | Dimethylformamide |
| EI | Electron Impact |
| AcOEt | Ethyl acetate |
| FAB POS | Fast Atom Bombardment/Positive ions detection |
| MS | Mass Spectrum |
| THF | Tetrahydrofuran |
| TSP | ThermoSpray |

Biological Assays

Background. It is known that, upon attachment to bone, an electrogenic $H^+$- adenosine triphosphatase (ATPase) is polarised to the osteoclast-bone interface. The pump transports massive quantities of protons into the resorption microenvironment to effect mobilisation of the bone mineral and to create the acidic pH required by collagenases to degrade the bone matrix.

The vacuolar nature of the osteoclast proton pump was originally recognised by Blair [H. C. Blair at al., Science, 245, 855 (1989)] and than confirmed by Bekker [P. J. Bekker et al., J. Bone Min. Res., 5, 569 (1990)] and Väänänen [K.K. Väänänen et al., J. Cell. Biol., 111, 1305 (1990)]. Evidence was based upon preparations of ruffled membrane fragments from avian osteoclasts (obtained from the medullar bone of calcium-starved egg-laying hens). The resulting membrane vesicles acidify in response to ATP, which is easily assessed by measuring the fluorescence quench of acridine orange, a weak base which accumulates into acidic compartments.

The biochemical pattern indicated that the osteoclast proton pump belonged to the vacuolar-like ATPases since proton transport was inhibited by N-ethylmaleimide (NEM), a sulphydryl reagent, and by bafilomycin $A_1$, a selective inhibitor of vacuolar $H^+$-ATPases [J. E. Bowman et al., Proc. Natl. Acad. Sci. USA, 85, 7972 (1988)], whilst it was not inhibited by ouabain, an inhibitor of $Na^+/K^+$-ATPases; sodium orthovanadate, an inhibitor of p-ATPases, or by omeprazole or SCH 28080, both of which are inhibitors of gastric $H^+/K^+$-ATPase [J. P. Mattson et al., Acta Physiol. Scand., 146, 253 (1992)].

It is known that specific inhibitors of vacuolar ATPases, such as bafilomycin $A_1$, are able to inhibit bone resorption in osteoclast cultures [K. Sundquist et al., Biochem. Biophys. Res. Commun. 168, 309–313 (1990)]

INHIBITION OF v-ATPase PROTON TRANSPORT IN MEMBRANE VESICLES

Preparation of crude bone microsomes from calcium-starved egg-laying hens.

Vesicles were prepared from medullar bone obtained from tibiae and femurs of egg-laying hens which were calcium-starved for at least 15 days. Briefly, bone fragments were scraped with a 24 scalpel blade, suspended in 40 ml of isolation medium (0.2 M sucrose, 50 mM KCl, 10 mM Hepes, 1 mM EGTA, 2 mM dithiotheitrol, pH 7.4) and filtered through a 100 µm pore size nylon mesh. The whole procedure was performed at 4° C. After homogenisation in a potter (20 strokes) in 40 ml of isolation medium an initial centrifugation (6,500×$g_{max}$20 min) was performed to remove mitochondria and lysosomes. The supernatant was centrifuged at 100,000×$g_{max}$ for 1 hr and the pellet was collected in 1 ml of isolation medium, divided into 200 µl aliquots, immediately frozen in liquid nitrogen and stored at −80° C. The protein content was determined using a Biorad colourimetric kit according to Bradford [M. Bradford, Anal. Biochem., 72, 248 (1976)]. For the proton transport assay, 5–10 µl of membranes were used.

Purification of osteoclast membranes. 1 ml of crude microsomal vesicles prepared above were applied (about 0.2 ml per tube ) on the top of a sucrose step-gradient consisting of 3.5 ml of 15%, 30% and 45% (w/w) sucrose in isolation medium and centrifuged at 280,000 $g_{max}$ for 2 hours (SW 41 Ti rotor). After centrifugation the 30–45% sucrose interfaces were collected, diluted approx. 20-fold in isolation medium and pelletted at 100,000 $g_{max}$ for 1 hour (SW 28 rotor). The pellet was then resuspended in 1 ml of isolation medium, aliquoted and frozen in liquid $N_2$ and stored at −80° C. until used.

Proton transport in membrane vesicles was assessed, semi-quantitatively, by measuring the initial slope of fluorescence quench of acridine orange (excitation 490 nm; emission 530) after addition of 5–20 µl of membrane vesicles in 1 ml of buffer containing 0.2 M sucrose, 50 mM KCl, 10 mM Hepes pH 7.4, 1 mM ATP $Na_2$, 1 mM CDTA, 5 µM valinomycin and 4 µM acridine orange. The reaction was started by addition of 5 mM $MgSO_4$. Results were expressed as the percent of the mean of two controls.

Inhibition of bafilomycin-sensitive ATPase activity was assessed in purified membrane vesicles by measuring the release of inorganic phosphate (Pi) during 30 min of incubation at 37° C. in a 96-well plate either in the presence or in the absence of bafilomycin Al. The reaction medium contained 1 mM ATP, 10 mM HEPES-Tris pH 8,50 mM KCl, 5 uM valinomycin, 5 uM nigericin, 1 mM CDTA-Tris, 100 uM ammonium molybdate, 0.2 M sucrose and membranes (20 ug protein/ml). The reaction was initiated by $MgSO_4$ (8-arm pipette) and stopped, after 30 min, by addition of 4 volumes of the malachite green reagent (96-arm pipette) prepared according to Chan [Anal. Biochem.

157, 375 (1986)]. Absorbance at 650 nm was measured after 2 min using a microplate reader. Results are expressed as $\mu$mol (Pi)×mg protein$^{-1}$×hour$^{-1}$ and, for each experiment, represent the mean±sem of triplicates.

PHARMACOLOGICAL DATA:
INHIBITION OF BAFILOMYCIN-SENSITIVE ATPASE IN CHICKEN OSTEOCLASTS

| Ex. No. | IC$_{50}$ ($\mu$M) ATPase assay |
|---|---|
| 4 | 7 |
| 6 | 1.1 |
| 15 | 22 |
| 20 | 15 |
| 26 | 3 |
| 30 | 30 |
| 33 | 4 |
| 34 | 0.17 |
| 37 | 30 |
| 44 | 0.62 |
| 45 | 14 |
| 46 | 0.59 |
| 49 | 4 |
| 50 | 0.62 |
| 51 | 1.1 |
| 53 | 1.2 |
| 54 | 0.34 |
| 56 | 0.07 |
| 57 | 1.6 |
| 59 | 0.13 |
| 60 | 0.85 |
| 62 | 1.4 |
| 64 | 0.15 |
| 65 | 17 |
| 66 | 0.1 |
| 67 | 1.3 |
| 70 | 0.12 |
| 71 | 0.53 |

INHIBITION OF BONE RESORPTION

In Vitro assays

1) Bone resorption can be assessed as described previously in the literature [T. J. Chambers et al., *Endocrinology*, 1985, 116, 234]. Briefly, osteoclasts were mechanically disaggregated from neonatal rat long bones into Hepes-buffered medium 199 (Flow, UK). The suspension was agitated with a pipette, and the larger fragments were allowed to settle for 30 sec. The cells were then added to two wells of a multiwell dish containing bone slices (each measuring 12 mm$^2$). After 15 min at 37° C. the bone slices were removed, washed in medium 199 and placed in individual wells of a 96-well plate. These were incubated for 24 hrs in a total volume of 2 ml of culture medium, consisting of 10% foetal calf serum in Hanks-buffered MEM, in the presence or absence of drug. The number of osteoclasts and bone resorption were quantified by confocal laser scanning microscopy (CLSM): the bone slices were fixed with 2% glutaraldehyde in 0.2M cacodylate buffer and the osteoclasts on each bone slice were stained for tartrate-resistant acid phosphatase. After counting the number of large, multinucleated, red-stained cells, the bone slices were immersed in 10% sodium hypochlorite for 60 min to remove cells, washed in distilled water and sputter-coated with gold. The entire surface of each bone slice was then examined in CLSM. The number and the size of the osteoclastic excavations, the plain area and the volume of bone resorbed was recorded. Results were expressed as mean pit number per osteoclast, mean area per osteoclast or mean volume per osteociast.

2) Inhibition of PTH-stimulated $^{45}$Ca$^{2+}$ release from pre-labelled foetal rat long bone. The assay is based on that described by Raisz (*J. Clin. Invest.* 44:103–116, 1965). Time-mated Sprague-Dawley rats were injected subcutaneously with 200 mCi of $^{45}$CaCl2 on the 18th day of gestation. On the following day, the foetuses were removed aseptically and the radii and ulnae were dissected free of adjacent soft tissue and the cartilaginous ends, and then cultured for 24 hr at 37° C. in BGJ medium containing 1 mg/ml BSA. The bones were then transferred to fresh medium containing the test compounds (0.1–50 $\mu$M) with and without PTH (12 nM) and were incubated for an additional 48 hr. The media were collected and the bones extracted to determine the mean % calcium release by scintillation counting. Results were expressed as the % inhibition compared to the amount of calcium released from cultures incubated with PTH alone In vivo assays Prevention of retinoid-induced hypercalcaemia. The method used was that described by Trechsel et al., (*J. Clin. Invest.* 80:1679–1686, 1987). Briefly, male Sprague-Dawley rats weighing 160–200 g (10 per group) were thyroparathyroidectomised and were treated subcutaneously with the retinoid Ro 13-6298 (30 $\mu$g/day) for three days and this was found to significantly increase blood serum calcium by 4–5 mg/100 ml. For inhibition of this effect, rats were treated simultaneously with test compounds i.v. or p.o. at 0.1–100 mg/kg, or vehicle and blood calcium was measured as described above, before treatment and one day after the last administration. Results were expressed as % inhibition with respect to vehicle-treated animals.

Prevention of bone loss in osteoporosis induced by ovariectomy and immobilisation. Seven groups of 10 Sprague-Dawley rats (200 g) underwent ovariectomy plus neurectomy of the sciatic nerve in the right hind limb, while one group was sham-operated according to the method described by Hayashi et al., (*Bone* 10:25–28, 1989). It was demonstrated that a steady-state was attained in the amount of trabecular bone lost 6–12 weeks after the operations. During a 6-week period, the operated animals received the test compounds (0.1–100 mg/kg p.o. u.i.d.), or vehicle. At the end of this treatment period, the animals were sacrificed and the tibia and femur of the hind limb removed. The tibia wet and dry weight were determined, and the density (displacement of water) and ashes content (total weight, calcium and phosphorous content) also measured. The femur were fixed in 10% formalin, de-mineralised in 5% formic acid and the coronal midshaft and longitudinal section of the distal metaphysis cut and stained with haematoxilin and eosin. Histomorphometric evaluation was made using a semi-automated image analyser (Immagini & Computer, Milan, Italy). In the distal metaphysis, the % trabecular bone area in the secondary spongiosa (which is the trabecular bone 1 mm from the epiphyseal growth plate to about 4 mm towards the midshaft giving a total area of 5 mm$^2$) and the number of trabeculae (according to Parfitt et al., *J. Bone Min. Res.* 2: 595, (1987)) were determined in all animals. In the midshaft, the medullary, cortical (CA) and total (TA) cross-sectional area was measured and the cortical index (CI) determined from the formula CI=CA/TA.

Prevention of bone loss in ovariectomised mature rats. The methodology employed is based on that described by Wronsky et al. [*J. Bone Min Res.*,6, 387 (1991)]. The bone loss, prevalently cancellous, occuring after the surgery is monitored by dual emission X-ray absorptiometry (DEXA) measurements of bone mineral density (BMD) of long bones and by HPLC measurements of urinary levels of products of bone collagen breakdown, such as the cross-link residues pyridinoline (PYD), deoxypyridinoline (DPD) and lysine glycosides, i.e. galactosylhydroxylysine (GHYL) and glucosyl-galactosyl-hydroxylysine (GGHYL).

Groups of 7–10 female Sprague-Dawley rats, about 90 days old and weighing 200–250 g are used. Rats are anesthetised by sodium pentobarbital (35 mg/kg i.v.), laparotomy is performed and ovaries are bilaterally removed. Wounds are adequately disinfected and sutured. A group is sham operated. During a 4-week experimental period, the operated animals receive test compounds in the appropiate vehicle (0.1–100 mg/kg p.o. u.i.d.) or vehicle alone. Twenty-four-hr urine samples are collected for PYD, DPD, GHYL and GGHYL determinations before and 2, 4, 8, 11, 15, 18, 22 and 25 days after surgery. The aliquots of urine are frozen and stored at −20° C. until HPLC analysis.

Before and at the end of the experimental period, the bone metaphyseal mineral densities of left distal femur and proximal tibia were evaluated in vivo using lightly anaesthetised animals. Results are expressed as % of prevention versus vehicle treated animals.

OTHER THERAPEUTIC UTILITIES:

The activity of the compounds of the invention for the other utilities mentioned herein may be determined by according to the following methods which are incorprated herein:

1. Antitumor activity may be determined according to the methods disclosed in published International Application, Publication number 93/18652; in particular the screen employed, experimental details and bibliography of M. R. Boyd et al., *Status of the NCI preclinical antitumor drug discovery screen; principles and practices of Oncology*, 3, issue 10, October 1989, Lippincott.

2. Antiviral activity may be assessed using the in vitro assays reported by H. Ochiai et al., *Antiviral Research*, 27, 425–430 (1995) or by C. Serra et al., Pharmacol. Res., 29, 359 (1994). Anti-HIV activity can be assessed as reported in the literature, for example by S. Velásquez et al., *J. Med. Chem.*, 38, 1641–1649 (1995)

3. Antiulcer activity may be assessed in vivo using the methods reported in the literature, for example, as described by C. J. Pfeiffer, *Peptic Ulcer*, C. J. Pfeiffer Ed., Munksgaard Publ., Copenaghen, 1971. In vitro assays for inhibition of vacuolization induced by *Helicobacter pylori* are described, for example, by E. Papini et al., *FEMS Microbiol. Lett.*, 113, 155–160 (1993)

4. Usefulness in treating Alzheimer's disease may be determined using models in vitro such as inhibition of amiloyd-β production as described in the literature by J. Knops et al., *J. Biol. Chem.*, 270, 2419–2422 (1995) or by models in vivo: such as the transgenic mouse model overexpressing human APP reported by D. Games et al., *Nature*, 373, 523–527 (1995).

5. Immunosuppressant activity can be assessed as reported in the literature, for example by M. K. Hu et al., *J. Med. Chem.*, 38, 4164–4170 (1995)

6. Antilipidemic activity can be assessed as reported in the literature, for example by E.A.L. Biessen et al., *J. Med. Chem.*, 38, 1846–1852 (1995). Antiatherosclerotic activity may be assessed by using animal models of atherosclerosis, such as the atherosclerotic rabbit model, which are reported in the literature, for example by R. J. Lee et al., *J. Pharm. Exp. Ther.*, 184, 105–112 (1973).

7. Angiostatic activity may be assessed using the methods reported in the literature, for example as described by T. Ishii et al., *J. Anibiot.*, 48, 12 (1995).

We claim:

1. A compound of formula (I):

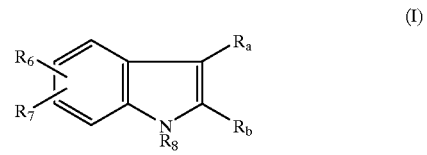

or a salt thereof, or a solvate thereof, wherein either: (i) Ra represents a group $R_5$ which is hydrogen, alkyl or optionally substituted aryl and Rb represents a moiety of formula (a):

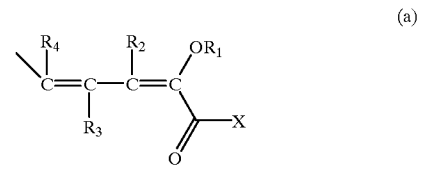

wherein X represents a hydroxy or an alkoxy group wherein the alkyl group may be substituted or unsubstituted or X represents a group $NR_sR_t$ wherein $R_s$ and $R_t$ each independently represent hydrogen, alkyl, substituted alkyl, optionally substituted alkenyl, optionally substituted aryl, optionally substituted arylalkyl, an optionally substituted heterocyclic group or an optionally substituted heterocyclylalkyl group, or $R_s$ and $R_t$ together may form a heterocyclic group; $R_1$ represents an alkyl or a substituted or unsubstituted aryl group; and $R_2$, $R_3$ and $R_4$ each independently represent hydrogen, alkyl, aryl or substituted aryl or (ii) $R_a$ represents a moiety of the above defined formula (a) and $R_b$ represents the above defined $R_5$;

$R_6$ and $R_7$ each independently represents hydrogen, hydroxy, amino, alkoxy, optionally substituted aryloxy, optionally substituted benzyloxy, alkylamino, dialkylamino, halo, trifluoromethyl, trifluoromethoxy, nitro, alkyl, carboxy, carbalkoxy, carbamoyl, alkylcarbamoyl, or $R_6$ and $R_7$ together represent methylenedioxy, carbonyldioxy or carbonyldiamino; and $R_8$ represents hydrogen, hydroxy, alkanoyl, alkyl, aminoalkyl, hydroxyalkyl, carboxyalkyl, carbalkoxyalkyl, carbamoyl or aminosulphonyl.

2. A compound according to claim 1, wherein Ra represents a group $R_5$ and Rb represents a moiety of formula (a).

3. A compound according to claim 1, wherein $R_1$ represents alkyl or substituted or unsubstituted phenyl.

4. A compound according to claim 1, wherein $R_2$, $R_3$ and $R_4$ each independently represent hydrogen, alkyl or phenyl.

5. A compound according to claim 1, wherein $R_6$ and $R_7$ each independently represents hydrogen, hydroxy, amino, alkoxy, optionally substituted phenyloxy, optionally substituted benzyloxy, alkylamino, dialkylamino, halo, trifluoromethyl, nitro, alkyl, carboxy, carbalkoxy, carbamoyl, alkylcarbamoyl, or $R_6$ and $R_7$ together represent methylenedioxy, carbonyldioxy or carbonyldiamino.

6. A compound according to any one of claims 1 to 5, wherein $R_8$ is hydrogen, methyl and t-butoxycarbonylmethyl.

7. A compound according to claim 1 wherein X represents $NR_sR_t$.

8. A compound according to claim 7, wherein $R_s$ and $R_t$ each independently represent hydrogen, alkyl, substituted alkyl, optionally substituted alkenyl, optionally substituted aryl, optionally substituted arylalkyl, an optionally substituted heterocyclic group or an optionally substituted heterocyclylalkyl group or $R_s$ and $R_t$ together represent a heterocyclic group.

9. A compound according to claim 1, wherein $R_t$ is hydrogen.

10. A process for the preparation of a compound of claim 1 or a salt thereof or a solvate thereof, which process comprises:

(a) for compounds of formula (I) wherein Ra represents hydrogen, alkyl or optionally substituted aryl and $R_b$ represents a moiety of the above defined formula (a), by reacting a compound of formula (II):

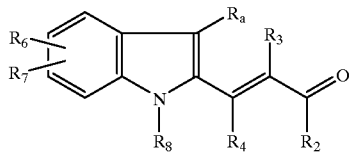
(II)

wherein $R_2$, $R_3$, $R_4$, $R_6$, $R_7$ and $R_8$ are as defined in relation to formula (I), with a reagent capable of converting a moiety of formula

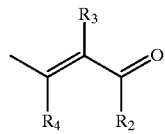

into a moiety of the above defined formula (a); or (b) for compounds of formula (I) where $R_a$ represents a moiety of the above defined formula (a) and $R_b$ represents hydrogen, alkyl or optionally substituted aryl, by treating a compound of formula (III):

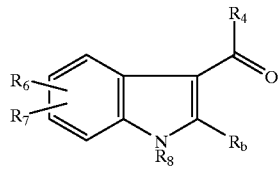
(III)

wherein $R_4$, $R_6$, $R_7$ and $R_8$ are as defined in relation to formula (I) with a compound of formula (IV):

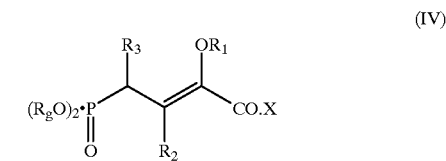
(IV)

wherein $R_1$, $R_2$, $R_3$ and X are as defined in relation to the compounds of formula (I) and $R_9$ is a $C_{1-4}$ alkyl group; and thereafter, as necessary, carrying out one or more of the following reactions:

(i) converting one compound of formula (I) into another compound of formula (I);

(ii) removing any protecting group;

(iii) preparing a salt or a solvate of the compound so formed.

11. A pharmaceutical composition comprising an effective amount of a compound of claim 1, or a pharmaceutically acceptable salt thereof, or a pharmaceutically acceptable solvate thereof, and a pharmaceutically acceptable carrier thereof.

12. A method for the treatment of osteoporosis and related osteopenic diseases in a human or non-human mammal, which comprises administering an effective, non-toxic, amount of a compound of formula (I) or a pharmaceutically acceptable solvate thereof, to a human or non-human mammal in need thereof.

13. A method for the treatment of: tumours, ulcers, autoimmune diseases, lipidemic disorders, for the treatment and/or prevention of hypercholesterolemic and atherosclerotic diseases, for the treatment of AIDS and Alzheimer's disease and for treating angiogenic diseases, in a human or non-human mammal, which comprises administering an effective, non-toxic, amount of a compound of claim 1 or a pharmaceutically acceptable solvate thereof, to a human or non-human mammal in need thereof.

* * * * *